(12) United States Patent
Bitoun

(10) Patent No.: US 11,006,828 B2
(45) Date of Patent: May 18, 2021

(54) MEASUREMENT OF OCULAR PARAMETERS USING VIBRATIONS INDUCED IN THE EYE

(71) Applicant: I SONIC MEDICAL CORPORATION, S.A.S., Paris (FR)

(72) Inventor: Pierre Bitoun, Paris (FR)

(73) Assignee: I SONIC MEDICAL CORPORATION, S.A.S., Paris (FR)

(*) Notice: Subject to any disclaimer, the term of this patent is extended or adjusted under 35 U.S.C. 154(b) by 166 days.

(21) Appl. No.: 15/326,564

(22) PCT Filed: Jul. 13, 2015

(86) PCT No.: PCT/IB2015/055297
§ 371 (c)(1),
(2) Date: Jan. 16, 2017

(87) PCT Pub. No.: WO2016/009334
PCT Pub. Date: Jan. 21, 2016

(65) Prior Publication Data
US 2018/0116512 A1 May 3, 2018

Related U.S. Application Data

(60) Provisional application No. 62/025,761, filed on Jul. 17, 2014.

(51) Int. Cl.
*A61B 3/16* (2006.01)
*A61B 3/10* (2006.01)
(Continued)

(52) U.S. Cl.
CPC ............ *A61B 3/165* (2013.01); *A61B 3/1005* (2013.01); *A61B 3/16* (2013.01); *G01S 7/4916* (2013.01); *G01S 17/58* (2013.01)

(58) Field of Classification Search
CPC ......... A61B 3/16; A61B 3/165; A61B 3/1005; G01S 17/58; G01S 7/4916; A01P 3/366
See application file for complete search history.

(56) References Cited

U.S. PATENT DOCUMENTS 2,519,681 A 8/1950 Mages
3,049,001 A 8/1962 Mackay et al.
(Continued)

FOREIGN PATENT DOCUMENTS

CN 1494864 5/2004
CN 101352333 1/2009
(Continued)

OTHER PUBLICATIONS

Agrawal, Ankur; "Laser Displacement Sensor Using Self-Mixing Effect"; School of Engineering and Science, International University Bremen, Germany; Fall 2004.
(Continued)

*Primary Examiner* — Patrick Fernandes
(74) *Attorney, Agent, or Firm* — Sheridan Ross P.C.

(57) ABSTRACT

Described is a system, method and apparatus for measuring a vibrational response in an eye for determination of ocular parameters such as intraocular pressure, corneal elasticity and scleral pressure. The method comprises positioning an air jet nozzle to direct an excitation stimulus at a single frequency to the apex of the eye along the optical axis of the eye; positioning a sensor to direct incident light at a fixed position of the eye distinct from the apex of the eye; exciting vibration in the eye with the excitation stimulus; directing incident light from the sensor to the fixed position of the eye; and detecting backscatter light from the eye with the sensor, to measure the vibrational response. Algorithms are used to calculate the ocular pressure from the vibrational response
(Continued)

of the cornea or sclera. The method does not require contact with the eye, and is reliable and accurate.

20 Claims, 21 Drawing Sheets

(51) Int. Cl.
*G01S 17/58* (2006.01)
*G01S 7/4912* (2020.01)

(56) References Cited

U.S. PATENT DOCUMENTS

| | | | |
|---|---|---|---|
| 3,070,087 A | 12/1962 | Sittel | |
| 3,181,351 A | 5/1965 | Stauffer | |
| 3,192,765 A | 7/1965 | Keiper | |
| 3,756,073 A * | 9/1973 | Lavallee | A61B 3/165 600/401 |
| 4,699,482 A * | 10/1987 | Utsugi | A61B 3/12 351/206 |
| 4,947,849 A | 8/1990 | Takahashi et al. | |
| 5,014,277 A | 5/1991 | Van Driel et al. | |
| 5,372,030 A * | 12/1994 | Prussia | A61B 3/165 209/509 |
| 5,833,606 A | 11/1998 | Haraguchi | |
| 5,838,439 A | 11/1998 | Zang et al. | |
| 6,885,438 B2 | 4/2005 | Deines | |
| 7,061,592 B2 | 6/2006 | Deines | |
| 7,201,720 B2 | 4/2007 | Cuzzani et al. | |
| 7,202,942 B2 | 4/2007 | Deines | |
| 7,268,705 B2 | 9/2007 | Kong | |
| 7,283,214 B2 | 10/2007 | Xu et al. | |
| 7,505,033 B2 | 3/2009 | Guo et al. | |
| 7,528,824 B2 | 5/2009 | Kong | |
| 7,543,750 B2 | 6/2009 | Kong | |
| 7,557,795 B2 | 7/2009 | Kong et al. | |
| 7,588,336 B2 | 11/2009 | Honda et al. | |
| 8,078,245 B2 | 12/2011 | Daly et al. | |
| 8,545,404 B2 | 10/2013 | Ishii et al. | |
| 2001/0032514 A1 | 10/2001 | Maruyama | |
| 2004/0008322 A1 | 1/2004 | Ogawa | |
| 2004/0109155 A1 | 6/2004 | Deines | |
| 2005/0062955 A1 | 3/2005 | Deines | |
| 2007/0097317 A1 | 5/2007 | Hayashi et al. | |
| 2007/0123761 A1 | 5/2007 | Daly et al. | |
| 2007/0263205 A1 | 11/2007 | Deines | |
| 2008/0242965 A1 | 10/2008 | Norris et al. | |
| 2010/0081940 A1 | 4/2010 | McKenna | |
| 2010/0134803 A1 | 6/2010 | Baier et al. | |
| 2010/0177300 A1 | 7/2010 | Kuwata | |
| 2010/0187449 A1 | 7/2010 | Schemmann et al. | |
| 2010/0281986 A1 | 11/2010 | Toal et al. | |
| 2011/0118585 A1 * | 5/2011 | Ishii | A61B 3/16 600/401 |
| 2011/0245649 A1 | 10/2011 | Luce | |
| 2013/0165763 A1 | 6/2013 | Huang et al. | |

FOREIGN PATENT DOCUMENTS

| | | |
|---|---|---|
| EP | 1121895 | 8/2001 |
| EP | 2236075 | 6/2010 |
| IT | 940012 | 10/1994 |
| WO | WO 99/024786 | 5/1999 |
| WO | WO 2002/002012 | 1/2002 |
| WO | WO 2002/095475 | 11/2002 |
| WO | WO 2003/001268 | 1/2003 |
| WO | WO 2005/058152 | 6/2005 |
| WO | WO 2006/066876 | 6/2006 |
| WO | WO 2010/058322 | 5/2010 |
| WO | WO 2010/113074 | 10/2010 |
| WO | WO 2010/116288 | 10/2010 |
| WO | WO 2010/136948 | 12/2010 |
| WO | WO 2010/144854 | 12/2010 |
| WO | WO 2010/149651 | 12/2010 |
| WO | WO 2011/004307 | 1/2011 |
| WO | WO 2011/008383 | 1/2011 |

OTHER PUBLICATIONS

Cattini, S. et al.; "Blood Flow Measurement in Extracorporeal Circulation Using Self-Mixing Laser Diode"; SPIE, 2010.
Cervino, A.; "Rebound Tonometry: New Opportunities and Limitations of Non-Invasive Determination of Introcular Pressure"; British Journal of Ophthalmology, vol. 90, Issue 12, Dec. 2006, pp. 1444-1446.
De Lucia, F. et al.; "Laser—self-mixing Interferometry in Gaussian Beam Approximation"; Optics Express, 2010.
Ducloux, O. et al; "A Magnetically Actuated, High Momentum Rate MEMS Pulsed Microjet for Active Flow Control"; Journal of Micromechanics and Microengineering, vol. 19, No. 11; Abstract Only.
Elsheikh, A. et al; "Mutiparameter Correction Equation for Goldmann Applanation Tonometry"; Opotometry and Vision Science; vol. 88, No. 1; Jan. 2011, pp. E102-E112.
Elsheikh, A. et al; "Assessment of Corneal Biomechanical Properties and Their Variation with Age"; Current Eye Research, vol. 32, 2007, pp. 11-19.
Eye Wiki Article; "Intraocular Pressure and Tonometry"; Retrieved from http://eyewiki.aao.org/IOP_and_Tonometry on May 1, 2014.
Giuliani, Guido and Donati, Silvano; "New Laser Vibrometer for Single- and Multiple-Point Measurements with Compact-Sized Optical Head"; Society for Experimental Mechanics, Inc.; Feb. 9-12, 2009.
Giuliani, Guido, Bozzi-Pietra, Simone and Donati, Silvano; "Self-Mixing Laser Diode Vibrometer"; Measurement Science and Technology; 14 (2003) 24-32.
Giuliani, Guido, Norgia, Michele and Donati, Silvano; "Self-Mixing Laser Diode Vibrometer for the Measurement of Differential Displacements"; SPIE vol. 7098, pp. 709814-1-709814-5.
Josephson; A.; "Goldmann Applanation Tonometry Versus I-Care Rebound Tonometry"; Optician, Jan. 16, 2009; found online at opticianonline.net.
Karmel, Miriam; "Clinical Update: Glaucoma"; Retrieved from http://www.aao.org/publications/eyenet/200505/glaucoma.cfm on Apr. 30, 2014.
Lafaut, A. et al.; "Is Pulse Synchronized Pneumotonometry More Reproducible Than Routine Pneumotonometry and More in Agreement with Goldmann Applanation Tonometry?"; European Journal of Ophthalmology, vol. 17, No. 2, 2007, pp. 178-182.
Lukashkin, A. et al; "A Self-Mixing Laser-Diode Interferometer for Measuring Basilar Membrane Vibrations Without Opening the Cochlea"; Abstract Only; Journal of Neuroscience Methods, vol. 148, Issue 2, Oct. 30, 2005; pp. 122-129.
Mangouritsas, G. et al; "Comparison of Goldmann and Pascal Tonometry in Relation to Corneal Hysteresis and Central Corneal Thickness in Nonglaucomatous Eyes"; Clinical Ophthalmology vol. 5, 2011, pp. 1071-1077.
Norgia, Michele, Giuliani, Guido and Donai, Silvano; "Self-Mixing Differential Laser Vibrometer"; Dipartimento di Elettronica e Informazione, Politecnico di Milano, Italy; ND.
Norgia, M. et al; "Frequency Compensation for a Self-Mixing Interferometer"; Abstract Only; Instrumentation and Measurement; vol. 59, Issue 5; May 2010, pp. 1368-1374.
O'Donnell, Matthew L. "An Introduction to Self-Mixing Interferometry With an Application to Vibrometry"; Abstract Only; Dec. 2008.
Paone, Nicola and Scalise, Lorenzo; "Advances in Self-Mixing Vibrometry"; SPIE vol. 4204 (2001), pp. 103-114.
Scalise, Lorenzo and Paone, Nicola; "Laser Doppler Vibrometry Based on Self-Mixing Effect"; Abstract Only; Jan. 30, 2002.
Srodka, W.; Goldmann Applanation Tonometry—Not As Good as Gold; Acta of Bioengineering and Biomechanics; vol. 12, Issue 2 2010, pp. 39-47.

(56) References Cited

OTHER PUBLICATIONS

Technology Offer; "Non Contact Vibration Measurements Using Self Mixing Laser Vibrometer"; Retrieved from Enterprise Europe Network on Feb. 1, 2011.
Tonnu, P-A. et al; "The Influence of Central Corneal Thickness and Age on Intraocular Pressure Measured by Pneumotometry, Non-Contact Tonometry, The Tono-Pen XL, and Goldmann Applanation Tonometry"; Br J Ophthalmol, 2005, vol. 89, pp. 851-854.
Wikipedia Article; "Interferometry"; retrieved from http://en.wikipedia.org/wiki/Interferometry on Aug. 30, 2010.
Zabit, U. et al. "Adaptive Self-Mixing Vibrometer Based on Liquid Lens"; Optics Letters, vol. 35, Issue 8, pp. 1278-1280.
International Search Report and Written Opinion for International (PCT) Patent Application No. PCT/IB2015/055297, dated Dec. 4, 2015.
International Preliminary Report on Patentability for International (PCT) Patent Application No. PCT/IB2015/055297, dated Jan. 17, 2017.
Partial Supplementary Search Report for European Patent Application No. 15821909.7, dated Mar. 9, 2018.
International Search Report and Written Opinion prepared by the United States Patent and Trademark Office dated Oct. 23, 25, for International Application No. PCT/IB2015/055297.
Official Action with English Translation for China Patent Application No. 2015800387888, dated Jan. 16, 2019, 18 pages.

\* cited by examiner

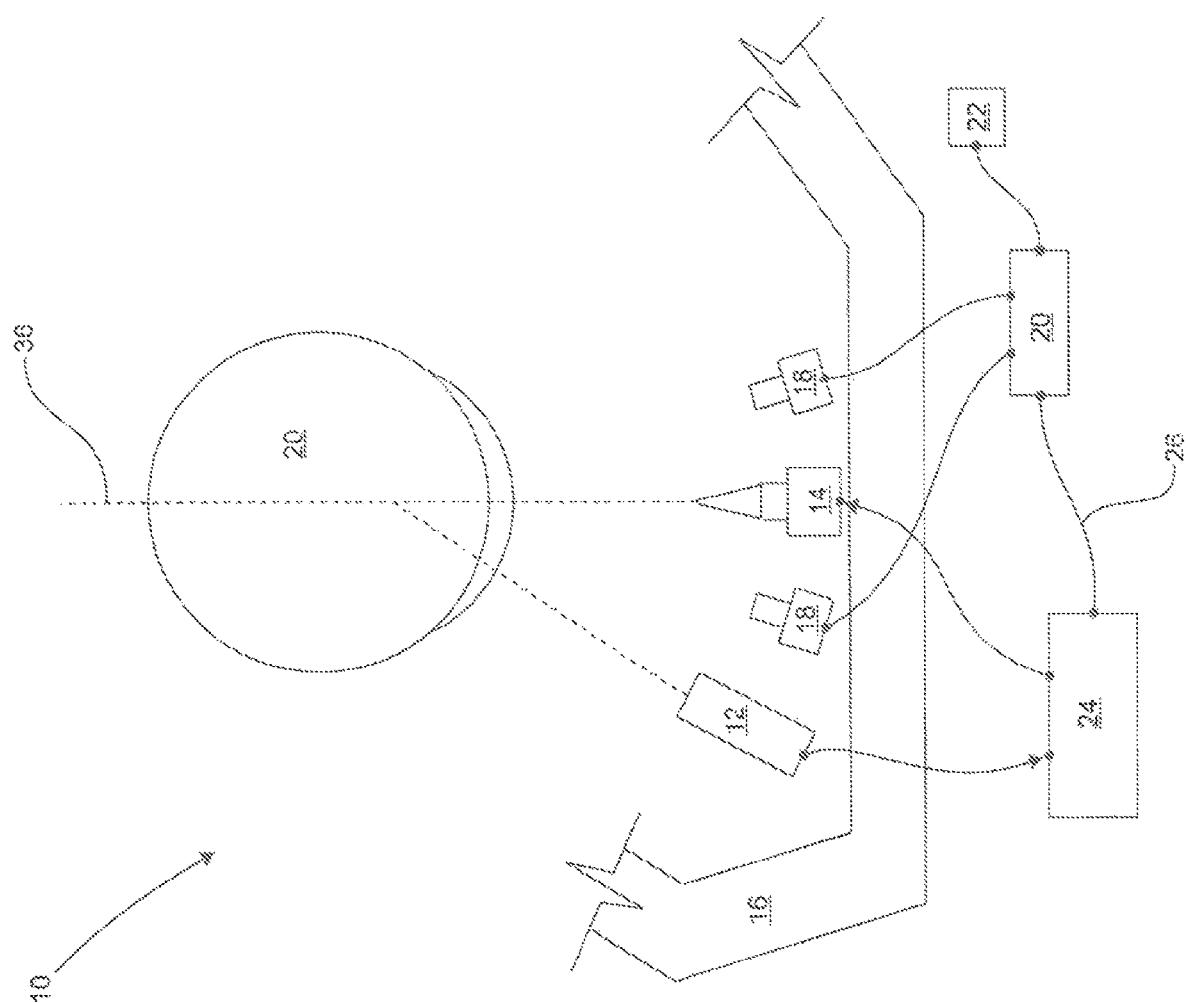

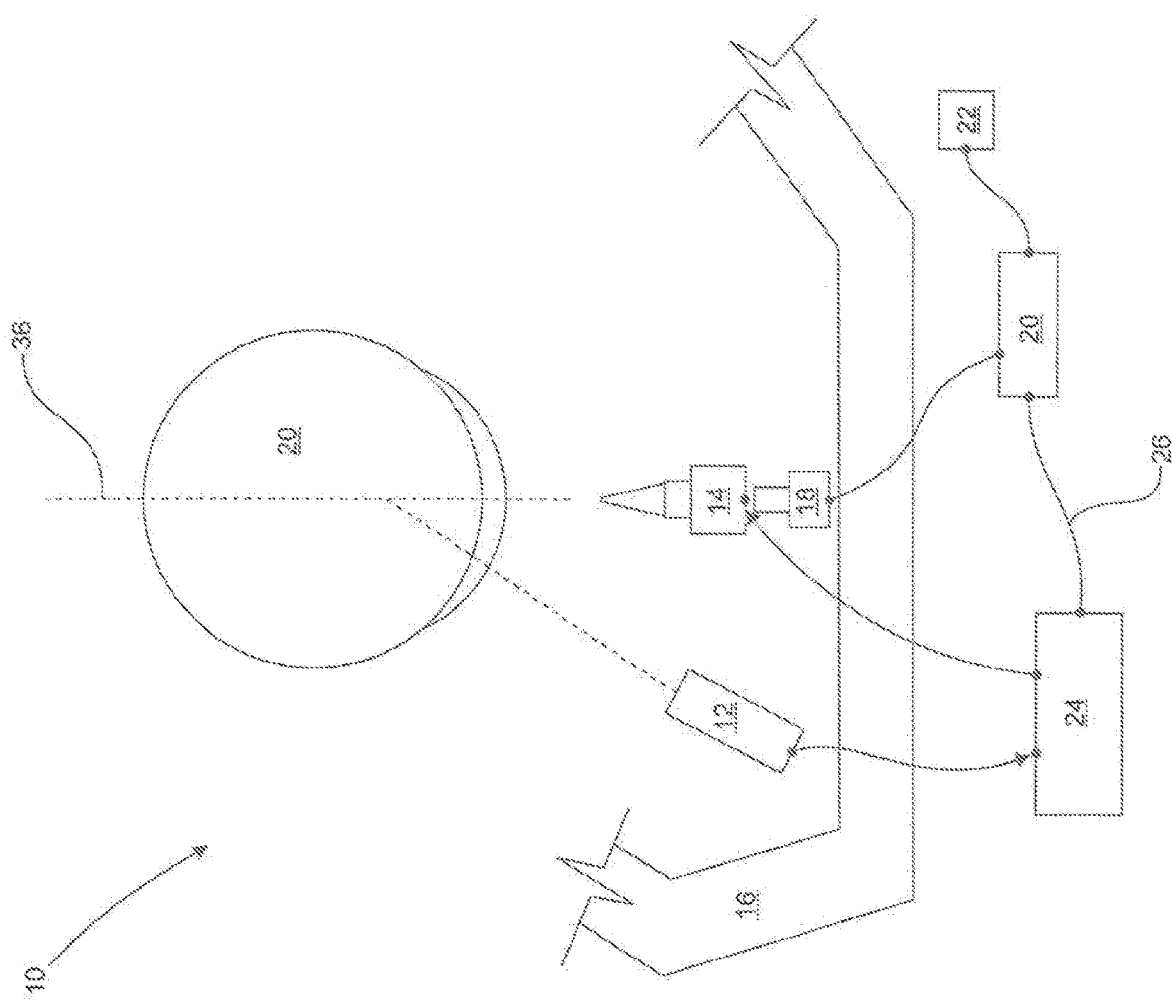

MEASUREMENT OF OCULAR PARAMETERS USING VIBRATIONS INDUCED IN THE EYE

CROSS REFERENCE TO RELATED APPLICATIONS

This application is a national stage application under 35 U.S.C. 371 and claims the benefit of PCT Application No. PCT/IB2015/055297 having an international filing date of 13 Jul. 2015, which designated the United States, which PCT application claimed the benefit of U.S. Provisional Application No. 62/025,761 filed 17 Jul. 2014, the disclosure of each of which are incorporated herein by reference.

FIELD

Embodiments of the invention are directed to apparatus and methods of use for non-contacting measurement of intra-ocular pressure in an eye and, more particularly, to the use of a sensor for the measurement of vibration induced in the eye, the intra-ocular pressure being related to the degree of vibration induced and the site where it is measured.

BACKGROUND

Measuring the intraocular pressure (IOP) of an eye is a measurement of the pressure of the fluid inside the front part of the eyeball. It is advantageous to monitor IOP as it is an indicator of the health of the eye. Excessively high IOP can be associated with retinal and optic nerve damage, such as in the case of glaucoma. Other diseases like uveitis can cause dangerously low pressure in the eyeball.

An eyeball may be deemed analogous to an elastic vessel filled with a fluid of a substantially incompressible nature. One can compare such an elastic vessel to a balloon having extensible walls wherein an increase in volume in the fluid produces a change in the internal pressure balanced by an expansion of the vessel wall. Fluids inside the eye circulate in a substantially continuous fashion and an increase in the influx of fluids normally accompanies a similar increase in the outflow of fluid. In cases where the outflow does not keep up with inflow, an increase in internal pressure and an expansion of the eye will occur. In situations where the rigidity of the eye's wall is increased, two effects are observed: increases in the internal pressure are greater per increase in fluid inflow; and a smaller overall expansion of the volume of the eye occurs.

The change in the expansion of the eye depends on the extensibility of the walls of the eyeball. The more extensible the wall, the greater the ability for the eye's volume to increase in response to a fluid volume change. The less extensible the wall, the less capable the eyeball is of coping with fluid volume change and consequently the more the fluid pressure will increase.

Typically, in medicine, pressure such as IOP is not measured directly because of the invasive nature and risks associated with placing a pressure sensor in the fluid of the eyeball. Therefore, determination of pressure is typically attempted using alternate, less invasive methods, some of which are used daily in clinic settings to indirectly measure eye pressure. Consequently, while the measurement of intraocular pressure directly, frequently or continuously, and non-invasively is desired, it is difficult to achieve.

Moderately invasive methods for measuring IOP are known. Devices known as "Contacting Tonometers" have been used extensively by the medical community for many years. Most common is the Goldmann applanation tonometer, which measures the force necessary to applanate a 3.06 mm diameter area of the cornea using a probe, and calculation of the IOP from such force. However, the popularity and attractiveness of contacting tonometers is offset by the need to have direct mechanical contact with the eye requiring anesthesia, and the measurements are both lengthy and cumbersome and involve risks of trauma, infection, allergy and discomfort. Further, the requirement for contact and the resulting deformation of the eye can introduce errors in the determination of IOP due to formation of tears, subjects with thin or thick corneas and changes in eye volume due to compression, and as a result the variance of the physical properties of the cornea. Such prior art devices are described in U.S. Pat. Nos. 2,519,681; 3,049,001; 3,070,087 and 3,192,765.

Various other attempts have been made to measure IOP discreetly or continuously by means of more indirect methods. Indirect methods have the advantage of being non-invasive, or at least less invasive than indentation and applanation tonometry.

Applanation tonometry has also been attempted using an air puff to avoid contact. As set forth in U.S. Pat No. 3,181,351, one such method introduces a sharp pulse of air onto the eye, while measuring the resulting deformation of the cornea at the site of air impact. Such indirect methodology usually suffers from several limitations: lack of accuracy and repeatability and a lack of absolute value in resulting measurements. This technique is not optimally precise or reproducible and also is dependent on central corneal thickness (CCT) as is well known to those in the art.

All applanation tonometers are based on applying a force on the apex of the cornea, which is near the optical axis of the eye, and measuring the resultant displacement of the cornea at this same apex.

Chromatic confocal sensors are used in a wide array of technologies to measure distance, displacement, velocity and surface roughness. Chromatic confocal sensors split white light into monochromatic stages (colors) by using a set of precisely aberrant lenses and focus these colors on a target. The essence of chromatic confocal imaging is the accurate detection of colors from light that is reflected back from target surfaces. A specific distance to the target is assigned to each color's wavelength, in a factory calibration. The phase shift induced by the aberrations on the different wavelengths going to, and reflected from, the target is used to perform an interferometric measurement of distance. Light reflected from the target surface is transmitted through a confocal aperture and onto a spectrometer which detects and processes the spectral changes and calculates distances.

Laser vibrometry or interferometry is a well-established technique for the non-contacting measurement of vibration within a solid object. The measurement is generally based upon the interference of coherent waves used to measure dimensions and vibrations. A typical Michelson interferometer configuration used in traditional Laser Doppler Vibrometers/Velocimeters (LDV's) requires a complex arrangement of various lenses, beam splitters and photodiodes.

As reported by Guiliani et al, in Measurement Science and Technology, Vol 14, 2003, p 24-32, self-mixing laser vibrometers based on a compact laser diode (LD) are known and are simple and versatile compared to conventional laser vibrometers. Such vibrometers rely upon a self-mixing interferometric configuration and on active phase-nulling accomplished through LD wavelength modulation. Light from the LD is focused on a remote reflective or diffusive target and a small fraction of the backscatter light is allowed to re-enter the LD cavity. The re-entered or re-injected light is coherently detected by the lasing field through a sort of mixing that generates a modulation of both the amplitude and the frequency of the lasing field. No optical interferometer is required external to the source resulting in a simple compact set-up. No external photodiode is required because the signal is provided by a monitor photodiode contained in the LD package. Operation on targets with rough diffusive surfaces is possible because the noise equivalent vibration of the scheme is very high, being a sort of coherent detection that easily attains the quantum detection regimen. Self-mixing interferometry is feasible with virtually all specimens of single-mode LD's. Furthermore, self-mixing laser interferometry is a versatile approach that has been deployed to measure displacement, distance, velocity and surface roughness.

Self-mixing laser vibrometry and chromatic confocal sensing have conventionally been applied to the measurement of vibrations in a variety of solid objects which typically have a reflective or diffuse surface capable of providing significant backscatter to the laser. The eye is not a "solid" object and reacts in a very complex way to an excitation stimulus.

In applying self-mixing laser vibrometry or chromatic confocal sensing to such non-solid objects as a human eyeball, one is faced with the problems associated with a substantially smooth, non-reflective surface which may only be capable of a limited backscatter of about 2-4%. Further, one is faced with the problems of transforming such vibration measurements to meaningful measures of pressure within the eye after filtering out spontaneous eye movements.

There is a need for better methods of measuring IOP using non-contact techniques. There is great interest in the development of non-contacting tonometers which utilize very sensitive vibration measurement technologies.

SUMMARY OF THE INVENTION

The present invention excites the vibration of the cornea using a very soft and fast micro air jet directed axially on the cornea precisely at the apex, which causes a very small perturbation of the cornea. The response of the cornea is measured with a sensor, at a different point on the cornea, away from the apex such as on the temporal side at a 45 degree angle below the horizontal equator of the cornea. Vibration amplitude or speed at this point of the cornea is less dependent on the actual force exerted to excite vibration and shows the response of the cornea to a vibration created at the apex site of excitation and measured at a distant point. The measurement of the resulting vibration is performed during the excitation of the cornea, and immediately after the excitation of the cornea, at critical times when the corneal response can be captured.

The force of the micro air jet is calibrated so that the corneal response is in the order of microns. As a comparison, most contact and non-contact applanation tonometers displace the cornea by approximately 100 microns or more.

The method described herein can be practiced using any sensor that is capable of reliably measuring the vibration response of the cornea. As examples, two different types of sensors that can be used to measure the vibration response will be described: a chromatic confocal sensor and a self-mixing laser vibrometer.

In one aspect the invention is a system for measuring a vibrational response in an eye for determination of ocular parameters that comprises:

an air jet nozzle directed at the apex of the eye along the optical axis, for providing an excitation stimulus at a single frequency to cause vibration in the eye; and a sensor for emitting incident light that is directed to a position on the eye removed a distance from the apex of the eye, and for receiving the backscatter light from the eye to measure the vibrational response of the eye to the excitation stimulus.

In one embodiment the incident light approaches the surface of the eye at a perpendicular angle. In one embodiment the incident light approaches the surface of the eye at an angle of 28+/−4 degrees between the optical axis and the axis of the incident light. In one embodiment the incident light approaches the surface of the eye on the temporal side of the apex of the eye. In one embodiment the distance from the apex of the eye is 2 to 6 mm. In another embodiment it is 5 to 6 mm.

In one embodiment the incident light approaches the surface of the eye at an angle of about 45 degrees below a horizontal axis of the eye. In one embodiment the position on the eye is remote from attachment points of musculature of the eye and supporting structure thereabout for obtaining maximum displacement of the eye in response to the excitation stimulus.

In one embodiment the air jet nozzle is positioned a distance from the apex of the eye that ensures that air from the excitation stimulus contacts the eye in the laminar portion of the air flow. In one embodiment the excitation stimulus has a duration of less than 15 milliseconds. In another embodiment it has a duration of less than 5 milliseconds. In yet another embodiment the excitation stimulus causes vibration of the eye in the order of microns.

In one embodiment the measuring of the vibrational response comprises measuring both a temporal response and an amplitude response to the excitation stimulus. In yet another embodiment the measuring of the vibrational response comprises measuring during and immediately after the excitation stimulus. In yet another embodiment the system further comprises a circuit board for calculating the ocular parameter from the vibration parameters.

In one embodiment the system is a system for measuring intraocular pressure, and the system further comprises an algorithm for determining the intraocular pressure from the vibrational response of the cornea. The algorithm may incorporate both age and gender of the patient.

In one embodiment the system is a system for measuring the elastic properties of the eye, and the system further comprises an algorithm for determining the elastic properties of the cornea from the vibrational response of the cornea.

In embodiments the system further comprises one axial camera or two or more cameras positioned on either side of the optical axis for stereoscopically monitoring the positioning of the eye to ensure the optical axis of the eye is coincident with the axis of the air jet nozzle. The system may further comprise an LED light positioned relative to the air jet nozzle for aiding in aligning the optical axis of the eye coincident with the axis of the air jet nozzle.

In one embodiment the sensor is a chromatic confocal sensor. In another embodiment the sensor is a self-mixing laser vibrometer. In one embodiment the self-mixing laser vibrometer further comprises means for maintaining the phase between the laser signal and the returned signal from cornea at a constant phase. The means for maintaining the phase between the laser signal and the returned signal from cornea at a constant phase may be a servo-feedback loop.

In one embodiment the self-mixing laser vibrometer further comprises a compensation circuit for maintaining the laser diode at a constant power with changes in current. In one embodiment the self-mixing vibrometer circuit is used in an open loop configuration and a modulation signal is introduced onto the laser signal from the target.

In another aspect the invention is a method for measuring a vibrational response in an eye of a patient for determining ocular parameters comprising:
positioning an air jet nozzle to direct an excitation stimulus at a single frequency to the apex of the eye along the optical axis of the eye;
positioning a sensor to direct incident light at a fixed position of the eye distinct from the apex of the eye;
exciting vibration in the eye with the excitation stimulus;
directing incident light from the sensor to the fixed position of the eye; and
detecting backscatter light from the eye with the sensor, to measure the vibrational response of the eye to the excitation stimulus.

In one embodiment, before exciting vibration of the eye, measurements of the eye are recorded by directing incident light from the sensor to the fixed position of the eye and detecting backscatter light from the eye with the sensor. In one embodiment the incident light approaches the surface of the eye at the fixed position at a perpendicular angle.

In one embodiment the incident light from the sensor approaches the surface of the eye at the fixed position at an angle of 28+/−4 degrees between the optical axis and the axis of the incident light. In one embodiment the fixed position is on the temporal side of the apex of the eye.

In one embodiment the fixed position is 2 to 6 mm from the apex. In another embodiment the fixed position is 5 to 6 mm from the apex. In one embodiment the incident light approaches the surface of the eye at an angle of about 45 degrees below a horizontal axis of the eye.

In one embodiment the air jet nozzle is further positioned a distance from the apex of the eye that ensures that the air from the excitation stimulus contacts the eye in the laminar portion of the air flow. In one embodiment the excitation stimulus has a duration of less than 15 milliseconds. In one embodiment the excitation stimulus has a duration of less than 5 milliseconds.

In one embodiment the sensor is a chromatic confocal sensor. In another embodiment the sensor is a self-mixing laser vibrometer.

In one embodiment the measuring of the vibrational response comprises measuring both a temporal response and an amplitude response to the excitation stimulus. In one embodiment the measuring of the vibrational response comprises measuring during and immediately after the excitation stimulus.

In one embodiment the ocular parameter is intraocular pressure, and the method further comprises the step of determining the intraocular pressure from the vibrational response of the cornea using an algorithm that incorporates both age and gender of the patient.

In one embodiment the ocular parameter is corneal elasticity, and the method further comprises the step of determining the corneal elasticity from the vibrational response of the cornea using an algorithm.

In embodiments the method further comprises positioning the eye with one axial camera or two or more cameras positioned on either side of the optical axis. In one embodiment the method further comprises aligning the optical axis of the eye coincident with the axis of the air jet nozzle with an LED light positioned relative to the air jet nozzle.

In one embodiment, before exciting the vibration of the eye with the excitation stimulus, the patient directs their gaze to a side-fixating LED. This method may further comprise determining intraocular pressure from the vibrational response of the sclera, using an algorithm that incorporates both age and gender of the patient.

In one embodiment of the method the patient is a mammal. The mammal may be a human, a mouse, a rat, a rabbit, a cat, a dog, or a horse.

In another aspect the invention is a method of measuring intraocular pressure in an eye of a patient comprising:
positioning an air jet nozzle to direct an excitation stimulus at a single frequency to the apex of the eye along the optical axis of the eye;
positioning a sensor to direct incident light at a fixed position of the eye distinct from the apex of the eye;
asking the patient to direct their gaze to a side-fixating LED;
exciting vibration in the eye with the excitation stimulus; and
detecting backscatter light from the eye with the sensor, to measure the vibrational response of the sclera to the excitation stimulus.

In one embodiment this method further comprises the step of determining the intraocular pressure from the vibrational response of the sclera using an algorithm.

In another aspect the invention is use of a chromatic confocal sensor to measure ocular pulse amplitude.

In another aspect the invention is use of a chromatic confocal sensor to measure corneal thickness.

BRIEF DESCRIPTION OF THE DRAWINGS

FIG. 1A is a schematic of an embodiment of a non-contact tonometer system described herein.

FIG. 1B is a schematic of another embodiment of a non-contact tonometer system described herein.

DETAILED DESCRIPTION

Figure 2A:
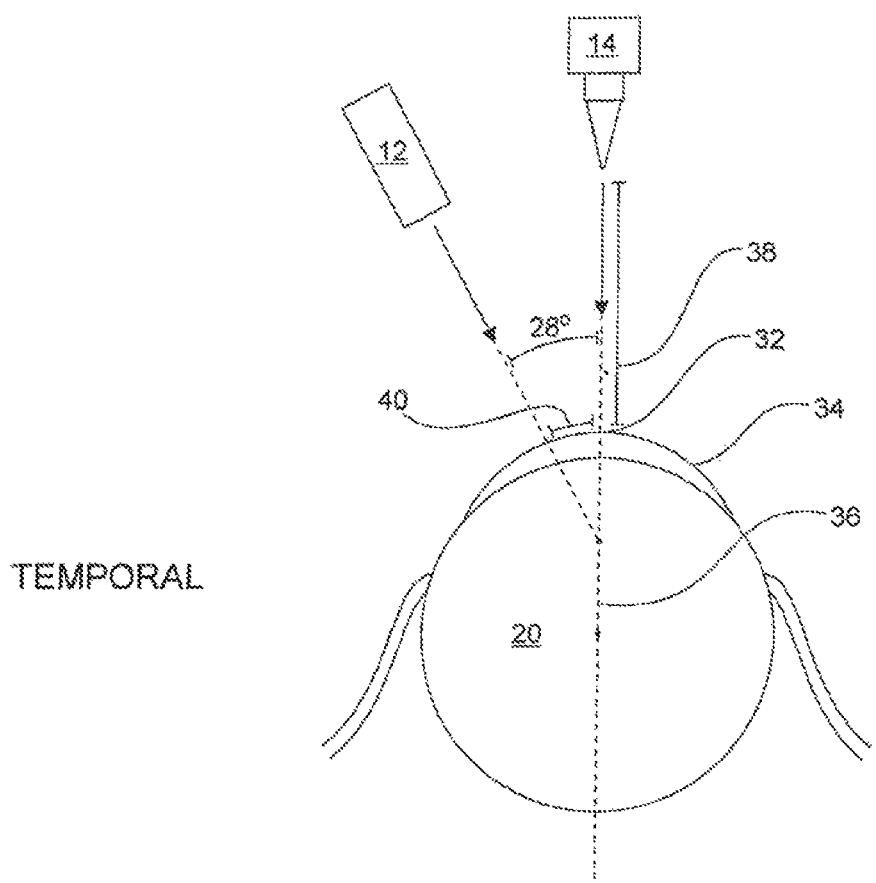
FIG. 2A is a top view of a human eye illustrating the positioning of an air jet nozzle at the apex of the cornea and a sensor relative to an optical axis of the eye.

Described herein is a method, system and apparatus for measuring parameters related to vibration of an eye which is excited to vibrate using a fast burst of air from a micro air jet nozzle. Specific positioning of a sensor and an air jet nozzle relative to the apex of the cornea has been used to optimize the excitation of the eye and the capture of limited backscatter of light, as the excitation at the apex of the cornea (or elsewhere on the eye) generates vibration at the site of measurement different from the apex. This method produces highly reliable and reproducible results, which can be used to inform a user of various optical parameters of the eye, such as the IOP measured on the cornea or on the sclera, and the dynamic elasticity of the cornea. Described herein as well is a method, apparatus and system for measuring optical pulse and corneal thickness.

The method, system and apparatus described herein can use any sensor that is capable of reliably measuring the very fast vibration response of the cornea or sclera. Such sensors are capable of very fast response rate to allow measurement of millisecond level displacements with a tenth of a micron precision. In some embodiments the sensor is a chromatic confocal sensor (hereafter "Confocal Sensor"). In other embodiments, the sensor is a self-mixing laser vibrometer (hereafter "Laser Sensor"). In the embodiments described herein the Confocal Sensor uses visible light from a 1 mw Xenon external illumination, while the Laser Sensor uses a 1550 nm wavelength, which is safe for human use as this wavelength doesn't penetrate the cornea. Some embodiments include using a MEMS sensor to measure distance.

The system, method and apparatus excite the eye along its optical axis at the anatomic apex of the cornea. The excitement causes vibration of the cornea, which is measured at a distance from the apex. Therefore, the points of excitation and measurement are physically distanced from one another, enabling the measurement of both a temporal response and an amplitude response to the excitation stimulus. Prior art methods, such as that described in U.S. Pat. No. 7,201,720 excite vibration and measure corneal response at the same point.

The system, method and apparatus use a quick air pulse at a single frequency to excite the apex of the cornea. This is different from prior art methods, such as that described in U.S. Pat. No. 7,201,720, which use a frequency oscillator to excite the cornea over a range of frequencies. In the present method, vibration amplitudes and times measured at a different site from the site of excitation inform the operator of the IOP. Compared to many known methods of measuring IOP that applanate the cornea by a hundred microns or about 20% of the corneal thickness, the method described herein excites corneal vibration by only a few microns. Therefore, it is relatively free from the influence of corneal thickness, and the method itself thus does not modify the very pressure that it is trying to measure.

Having reference to FIG. 1A, an embodiment of the system 10 comprises a sensor 12 and air jet nozzle 14 which are mounted to a rigid support frame 16. The support frame is capable of translation about the x, y and z axes for positioning the air jet nozzle and the sensor relative to an eye 20. The entire system can be rotated by 90° to enable measurement of IOP in both eyes.

In this embodiment two digital stereoscopic cameras 18 are mounted to the support frame 16 on either side of the optical axis, and they aid in ensuring correct stereo positioning of the components of the tonometer relative to the eye. The air jet 14 comprises an LED to provide a point of fixation for the patient, and light from this LED reflects onto the cornea. The reflection is used by the stereoscopic cameras to centre the LED reflection on the eye, and hence, the air jet nozzle. A two-camera configuration is useful when the sensor is a Laser Sensor. In other embodiments a single camera may be used to aid in centring, for example when the sensor is a Confocal Sensor. Particularly useful cameras include Basler ace® series cameras. In some embodiments the system includes an eye tracking device mounted on the air jet nozzle to automatically assist with centring of the nozzle on the optical axis. The eye tracking device is a system of four LEDs and four light sensors positioned at the four corners of a square surface. The four sensors must record equal reflected light intensity from the cornea when the device is centered appropriately on the eye, or the device moves into such a position to restore this balance light input.

If a laser interferometer is used, an LED is aimed at the iris on the lateral side and the reflection on the iris is measured using light sensors to calculate distance between the LED and the EYE by triangulation as is well known to those of the art. This is used to position the laser device at proper distance from the eye.

In another embodiment the system uses a Basler Dart bare board camera in the axial position behind the air jet 14, as shown in FIG. 1B. Image processing well known to those of the art allows tracking of the reflections of 2 illumination LEDs and of the pupil edge in order to automatically center the machine on the optical axis. This allows the device to automatically monitor and validate the centring of the air micro jet on the optical axis and eliminates the need to use image visualization to allow the user to center the machine.

The system further comprises electronics for controlling the air jet nozzle and the sensor, means for obtaining vibration data from the sensor for ultimately determining the IOP of the eye. Operation of the tonometer is automated through use of a computer 20, such as a personal computer (PC) and appropriate software connected thereto. The computer 20 receives video signals from the stereoscopic cameras 18. A frame grabber captures digital still frames from the cameras' outputs which are displayed on a screen 22 and to assist with correct positioning of the eye 20 relative to the tonometer. Analog signals, being reference signals for the excitation time and vibration amplitudes from the sensor 12, are received from the sensor by an acquisition module 24 which is connected to the computer 20 through a USB connection 26. Control signals are generated in the acquisition module 24 for actuating the air jet nozzle 14 piezo electric for providing a burst of air and for powering the LED. The computer interface further allows the operator to identify the patient and to permit display of temporal and spectral signals acquired during a measurement sequence. The signals are then processed using an algorithm to calculate IOP from the vibration amplitude and time response of the cornea or sclera. The algorithm incorporates both age and gender of the patient to perform optimally.

Positioning of Components of the System Relative to Eye

It has been determined that in order to obtain substantially maximum vibration of the human eye, an excitation air burst is directed to a fixed position on the cornea which is remote from attachments points of musculature which support the eye. The resulting vibration measurement site is also at a point distant from attachment points of musculature which support the eye, and removed from the site of excitation.

Figure 2B:
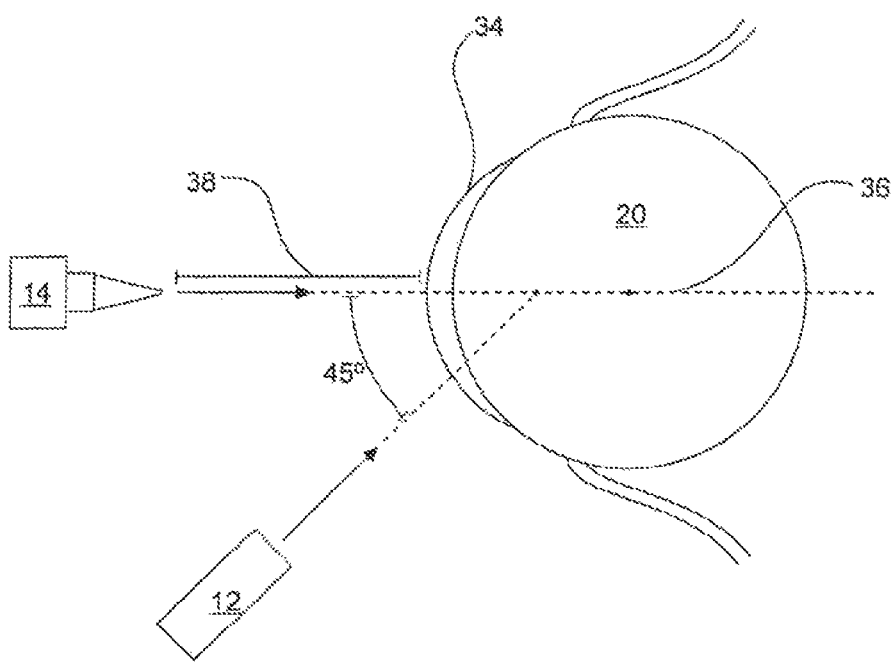
FIG. 2B is a side view of the eye of FIG. 2A illustrating the positioning of the air jet nozzle and a sensor relative to the optical axis of the eye.

FIGS. 2A and 2B, show one fixed position for the sensor 12 and air jet 14, which has been determined to achieve maximum vibration. FIG. 2A shows an air jet 14 directed at the apex 32 of the cornea 34 on the optical axis 36 of an eye 20 at a distance 38 axially from the apex of the cornea. This axial distance 38 depends on the pressure of air ejected from the air jet, and is selected so that the air that contacts the cornea is in laminar portion of the air jet flow. In some embodiments this distance is about 10 mm (1 cm).

In this embodiment the sensor 12 is directed at the eye so that incident light from the sensor contacts the eye at a distance 40 of about 2-6 mm, preferably about 4-6 mm or 5-6 mm, away from the apex at a 45 degree angle below the horizontal equator of the cornea on the temporal side T of the eye (see FIG. 2B). This constitutes about a 28 degree angle between the optical axis and the axis of the incident light (which in most embodiments is the longitudinal axis of the sensor). This angle depends on both the distance from the cornea and the properties of the sensor itself. The range is about +/−4 degrees in different embodiments herein used. The distance between the site of contact of the sensor's incident light and the site of excitation depends on the pressure of the air pulse from the air jet—the further away from the site of excitation, the greater the pressure needed to produce a measurable vibration.

The 45 degree angle below horizontal allows for smoother and faster flipping of the device from right to left eye position. However, persons of skill in the art would recognize that the cornea has a relatively round surface, and therefore that the sensor can be positioned so that the incident light contacts the cornea at any point around the apex of the cornea provided that it is a distance of about 2-6 mm, preferably about 4-6 mm or about 5-6 mm, away from the apex, which constitutes about a 28+/−4 degree angle between the optical axis and the axis of the sensor's incident light. Accordingly, in some embodiments the incident light from the sensor 12 is directed at the eye at a distance 40 of about 2-6 mm, preferably about 4-6 or about 5-6 mm, away from the apex at a 45 degree angle below the horizontal equator of the cornea on the nasal side of the eye. In other embodiments the incident light from the sensor 12 is directed at the eye at a distance 40 of about 2-6 mm, preferably about 4-6 or about 5-6 mm either temporally or nasally, at a 45 degree angle above the horizontal equator of the cornea. The positioning of the sensor is impacted by the anatomy of the face and eyes, and by the technological feasibility of manufacturing a tonometer with components in the desired positions. The Applicant currently favours the positioning of the sensor as shown in FIGS. 2A and B, however in other embodiments an alternative position may be selected.

The angle of 45 degrees below or above the horizontal equator is furthest from insertion points of muscles holding the eye and is thus a more favorable but non-exclusive embodiment using the smallest excitation pressure to allow a comfortable use on the patient.

FIG. 2B is a side view showing the position of the air jet 14 and its distance 38 from the apex of the cornea. The incident light from sensor 12 is on a plane below that of the air jet 14 a 45 degree angle below the horizontal equator of the cornea on the temporal side. The distance of the sensor from the cornea is not critical and can be different between different sensors. The distance depends on the optics and methods of use.

As is known for self-mixing laser vibrometers, backscatter received by the laser vibrometer results in a modulation of the laser diode intensity. This is representative of the vibration amplitude of the eye which, in turn, is affected by intraocular pressure of the eye. Applicant measured the backscatter from the human cornea and it is only 2-4% of the incident near infrared light at 1550 nm. In chromatic confocal sensing, different wavelength components of white light are imaged on the cornea. The dominant wavelengths in the light backscattered to the detector are representative of the vibration distance amplitude of the corneal surface.

The sensor is positioned at an optimal angle to capture this limited backscatter from the relatively smooth surface of the cornea of the eye which absorbs most of the light energy. To this end, the angle of incidence is important and the incident light is radial (i.e., normal or perpendicular) to the surface of the cornea, aiming at the centre of the corneal arc or sphere 42. This achieves maximum detection of the backscatter light.

Sensors

The sensors used in the method, system and apparatus described herein measure the variations of distance from the cornea to its optics by using the reflected light from the surface of the cornea and the time of response. The low surface reflectivity of the cornea of 2-4% requires that the incident light be fully normal i.e., perpendicular, to the surface tangent at the point of measurement. To improve reflectance from the cornea, and the signal to noise ratio, ophthalmic drops which enhance reflection of light from the cornea may be used, for example the drops described in U.S. patent application Ser. No. 14/037,211, which is incorporated herein in its entirety.

Self-Mixing Laser Vibrometer

Figure 3:
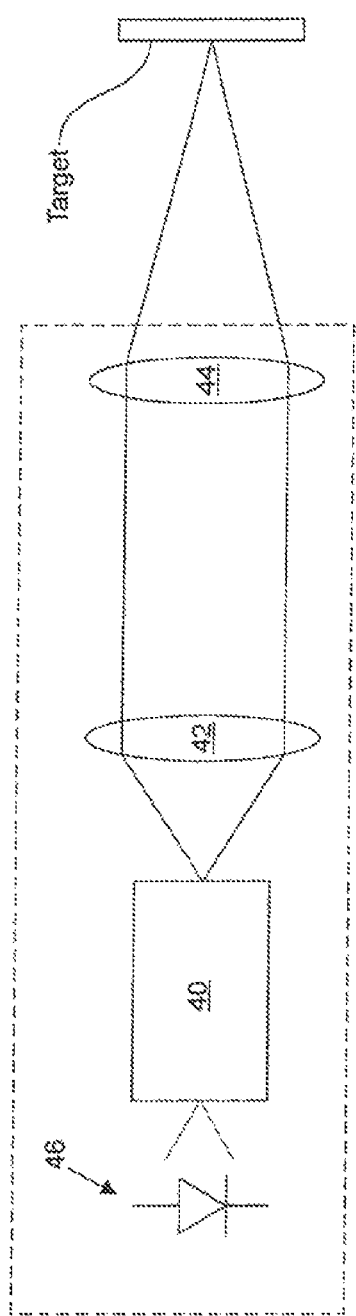
FIG. 3 is a schematic illustrating components of a self-mixing laser vibrometer.

Self-mixing laser vibrometers are well-known to persons of skill in the art and typically are a simple, compact apparatus comprising few components. The vibrometer typically comprises the laser diode 40, an objective lens 42, a focusing lens 44 and a monitor photodiode 46 (see FIG. 3). Systems according to the Laser Sensor embodiments of the invention are relatively simple and small. The Laser Sensor does not require the complex arrangement of various lenses, beam splitters and photodiodes found in conventional vibrometers.

In embodiments, the Laser Sensor comprises an infrared (IR) diode 40 (about 1550 nm), which was selected as it produces an incident beam which is safe for use on the human eye. A standard 6 mw 1550 IR Laser diode can be used such as Mitsubishi ML925B45F or equivalent (available from Mitsubishi or Thorlabs).

The Laser Sensor further comprises a photodiode 46 which monitors the laser diode 40 output. In order to reliably and reproducibly measure the parameters of displacement of the eye, the sensitivity of the photodiode is optimized to detect the limited backscatter from the cornea of about 2-4%.

Figure 5:
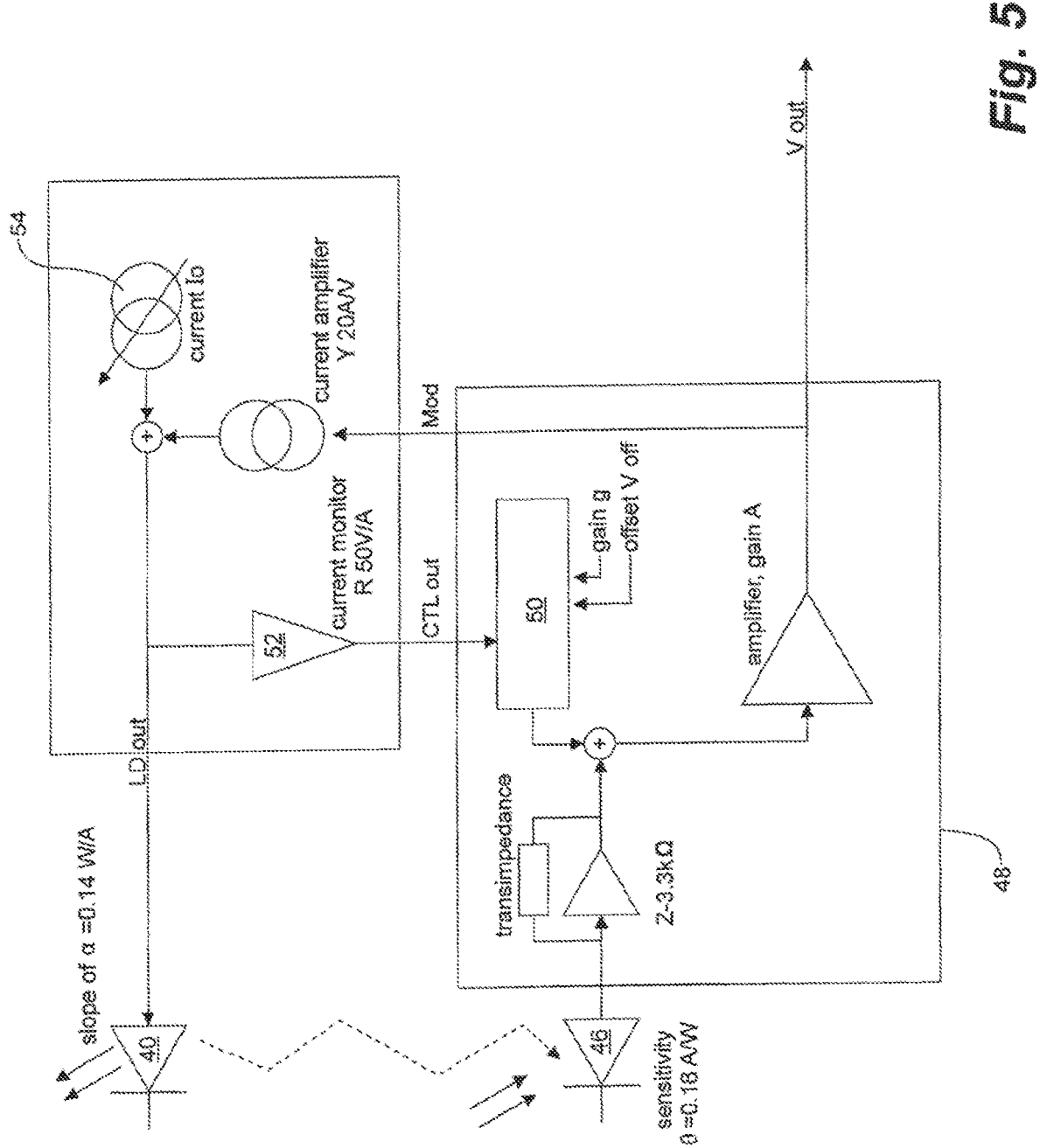
FIG. 5 is a schematic illustrating a servo-feedback loop and compensation circuit for the self-mixing laser vibrometer according to an embodiment of the invention.

In an embodiment, as shown in FIG. 5, the output of the laser diode is phase-locked using a servo-feedback loop 48 such as suggested by Guiliani et al in "Self-mixing laser diode vibrometer"; Measurement Science and Technology 14, (2003) pp 24-32, incorporated by reference herein in its entirety. The interferometer phase is typically locked to half a fringe. The electronic servo-feedback loop 48 compensates for slow phase variations in diode wavelength caused by environmental and thermal fluctuations. The servo-feedback loop 48 essentially monitors the power and changes the current fed to the laser diode 40 so as to keep a constant phase.

The feedback loop is also used to compensate for interferometric phase variations that are caused by the displacement of the target itself, referred to as "active phase-nulling", for expanding the dynamic range of the vibrometer. As the target moves away from the laser diode 40, the laser diode wavelength is suitably increased so as to keep a constant number of wavelengths in the path between the laser diode and the target.

Further, a compensation circuit 50 is provided to compensate for increases in the power of the diode when the current is increased. The properties of the compensation circuit are offset and gain. The circuit utilizes a summing inverter amplifier whose gain can be adjusted, such as by using a potentiometer. The outputs from the current supply 54 to the diode are fed to the amplifier 52 and an offset voltage is provided by a second amplifier also adjustable by means of a potentiometer. The compensation circuit is set using iteration and once set, the loop gain can be set and the loop locked.

The laser diode electronic control system can be implemented in various Doppler modes (constant current or constant power) or in phase locking mode (like described above (Giuliani type), these various implementations each presenting their own advantages and disadvantages in terms of stability, thermal sensitivity and cost. The power supply for Doppler modes of operation can be a standard external supply with transformer and filtered rectifier. Electronic control circuit includes a transimpedance amplifier, high pass and low pass filters, adapters and electronic components such as potentiometers for offset and gain control and others well known to those of the art. In this particular embodiment the self-mixing vibrometer circuit is used in an open loop configuration in order to introduce a modulation signal onto the laser signal from the target.

Modulation

The Laser Sensor requires separation of current from amplitude. The reflected light entering the laser cavity causes a perturbation of the laser, which impacts both current and amplitude, and these two have to be split. If there is too much movement of the eye, current and amplitude cannot be separated. In closed loop systems, current and amplitude have to be separated and this does not work well in the method described herein. Therefore the Applicants are using an open loop, which avoids having to deal with current, by introducing a modulation/demodulation which is superimposed on top of the signal.

A moving mirror placed in the beam of the reflected light from the target is moved by a piezo electric actuator such as a Cedrat model APA 100M (Cedrat Corp. Grenoble France) in order to introduce a modulation of the signal before it is fed back into the laser diode cavity. This allows separation of the phase from the amplitude of the current and thus allows, after demodulation and signal processing, the isolation of the pure target displacement signal as one skilled of the art can well understand.

Chromatic Confocal Sensor

Figure 4:
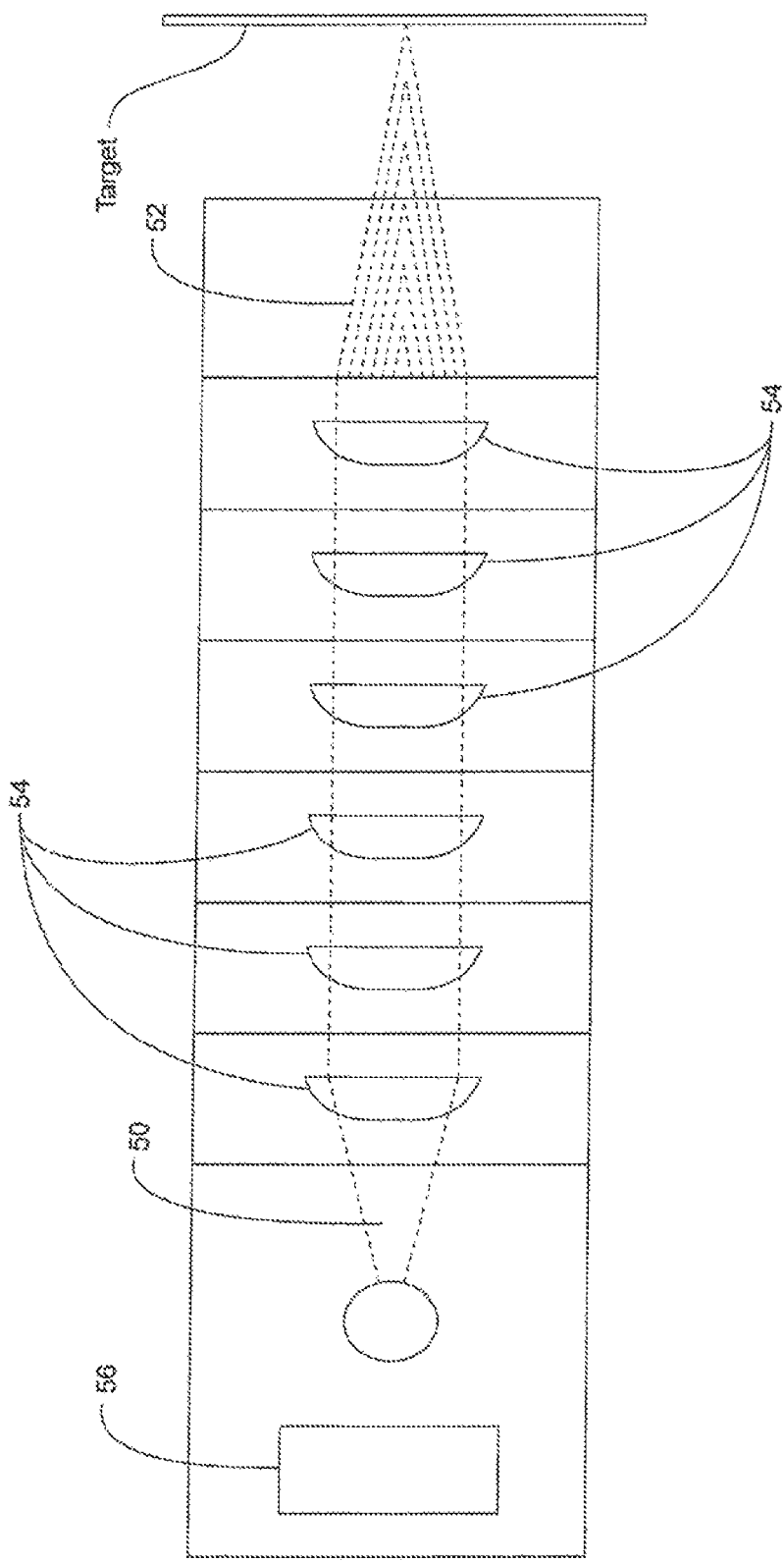
FIG. 4 is a schematic illustrating components of a chromatic confocal sensor.

Chromatic confocal sensors are well known in the art and are used in a wide array of technologies to measure distance, displacement, velocity and surface roughness. Having reference to FIG. 4, chromatic confocal sensors split white light 50 into monochromatic stages (colors) 52 by using a set of precisely aberrant lenses 54 and these colors are focused on a target. Light reflected from the target surface is transmitted from the probe, through a confocal aperture and onto a spectrometer 56 which detects and processes the spectral changes and calculates distances therefrom.

In an embodiment the Chromatic Sensor used is the confocal displacement sensor IFS 2405-3, obtained from Micro-Epsilon®, Germany using an external Xenon light. This sensor allows measurement of distances that differ by as little as $\frac{1}{10}^{th}$ of a micron. This sensitivity level is important, as the corneal displacement is very small due to a very small air jet excitation and the distance from the excitation site at which it is measured.

Important for the accuracy and reliability of the methods described herein using a Confocal Sensor is that the amount of reflected signal detected by the sensor is sufficiently high. In the embodiment of the Confocal Sensor used by the Applicants, about a 10% light level calibration needs to be detected by the meter in the sensor, in order to provide an accurate and reliable signal. Again, because the eye reflects only about 2 to 4% of the incident light, it is important that the sensor be positioned normal to the surface to the cornea, to maximize the amount of reflected light.

Each sensor is used according to manufacturer's instructions. The sampling frequency of the acquisition used herein was 10 kHz but can be used up to 25 kHz. About 3,000 points are thus acquired during the corneal response signal to the air jet.

Air Jet Nozzle

Air jet nozzles are conventionally used in applanation tonometry wherein the air jet is used to applanate or flatten the cornea. A micro air jet nozzle of about 1.5 mm outer diameter was selected as a means for exciting vibration in the eye because a strong pressure can be exerted on the eye using laminar flow. Further, the air jet avoids disturbing the patient with the loud sound which would be associated with a larger air jet that is also sufficiently strong to induce the vibrations measured herein.

In embodiments, a single burst of air is used over a total excitation time of less than about 15 milliseconds (ms), and preferably about 5 ms. In one embodiment, a total excitation time of 14 milliseconds duration is used (three ms on ramp, plateau of ten ms and off ramp of one ms). In another embodiment, a total excitation time of 5 milliseconds duration is used (three ms on ramp, plateau of one ms and off ramp of one ms). In another embodiment, a total excitation time of about 12 milliseconds is used (one ms on ramp, plateau of 10 ms and off ramp of one ms). Thus, the excitation stimulus has a duration of less than about 15 ms, preferably about 5 ms with a one ms on and off ramp and a 3 msec plateau.

The pressure of the single burst of air is sufficient to cause vibration of the cornea at the site of measurement, in the order of about one micron, which is generally so low as to be nearly imperceptible to the patient. In embodiments, the inlet pressure into the piezo chamber is 1,000 to 1,500 millibars (14 to 22 PSI), with the outlet pressure being much smaller.

As mentioned above, the micro air jet nozzle is positioned a distance from the apex of the cornea. This distance is selected based on the pressure of the air exiting the air jet nozzle. In particular, the air that reaches the cornea is preferably in a laminar as opposed to turbulent flow pattern. As the air jet nozzle is moved further away from the cornea, there is an increased likelihood of turbulent flow (i.e., eddie currents), which is undesirable. The distance of the air jet from the apex therefore is depends on the size of the air jet and the pressure of the air released, and is selected to ensure that the air contacts the cornea in the laminar portion of the air flow.

To calibrate the force of the air jet emitted from the micro air jet nozzle, a very small (15 mm diameter) sensitive microphone is positioned at the same distance from the air jet nozzle as the air jet nozzle is from the corneal surface. Another means of measuring the force of the air jet is a pressure gauge. The force applied to the eye needs to be sufficient to provide a reliable and readable vibration signal yet be imperceptible by the patient. This appropriate signal is determined by using increasing pressure until a vibration signal can be measured by the sensor.

In preferred embodiments the excitation pressure (pressure of the air as it leaves the pressure generator) is 800 mbars (11.4 PSI) for the first measurement. If the IOP is above 20 mmHg the resultant signal may not have sufficient amplitude to provide a reliable measurement, thus a second pulse at 1500 mbars (21.3 PSI) may be used to obtain adequate signal amplitude to accurately measure IOP.

Figure 8:
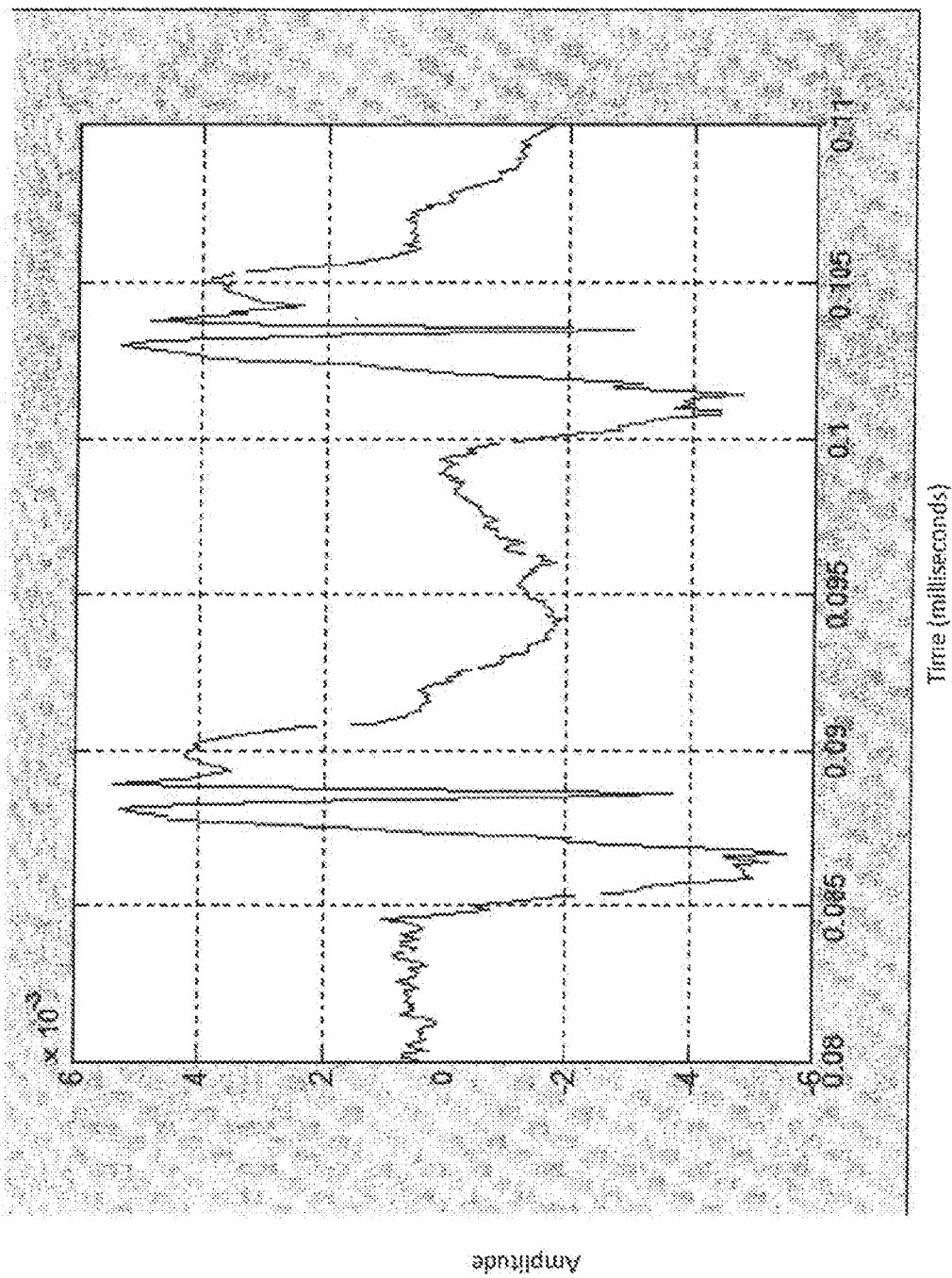
FIG. 8 is an example showing the repeatability of two pulses observed after two separate micro air jet excitations.
Figure 9:
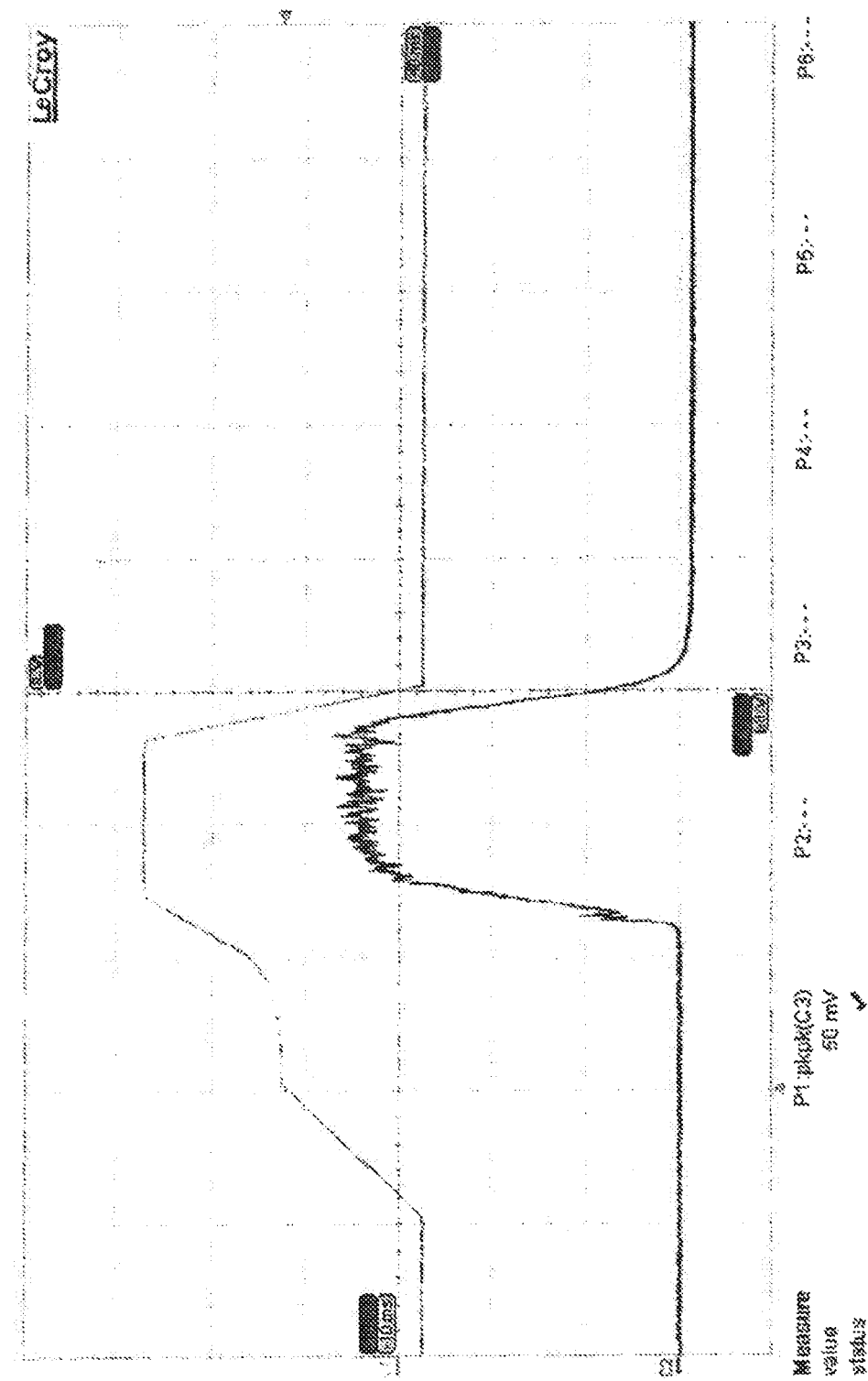
FIG. 9, top section, is a LeCroy oscilloscope electrical signal command generated to control the micro air jet over time; bottom section is a microphone tracing of the air jet response. This graph shows for the air jet, an on ramp that is about 11 milliseconds long, and the plateau is about 6 milliseconds long. The inlet pressure during the plateau period of the air jet was 600 mbars as measured by the manometer on the incoming fluid line. C1: F, BwL, DC1M, 2.00 V/div, 0.0 mV ofst; C2: F, BwL, DC1M, 2.00 V/div, −6.020 V. 0 ofst; Tbase −15.0 ms, 5 ms/div, 100 kS, 2.0 MS/s; Shutter C1 DC, Stop 2.5 V, Edge Positive.

As previously mentioned, vibration of the cornea is measured during the excitation and immediately afterwards (that is, within 10 to 20 msec, or less than 20 msec after shutoff of the airpulse). The cornea exhibits a vibration in response to the end of the excitation (see FIG. 8) and the amplitude of this vibration and time delay of this vibration from the onset of excitation are measured as well.

The air jet nozzle can be driven to produce the burst of air in a number of ways, such as using a chopper, a MEMS device, an electromagnetic system or a piezoelectric actuator. In the case of a chopper, the planarity of the rotating wheel is carefully controlled to avoid distortion of the air jet characteristics.

Figure 6:
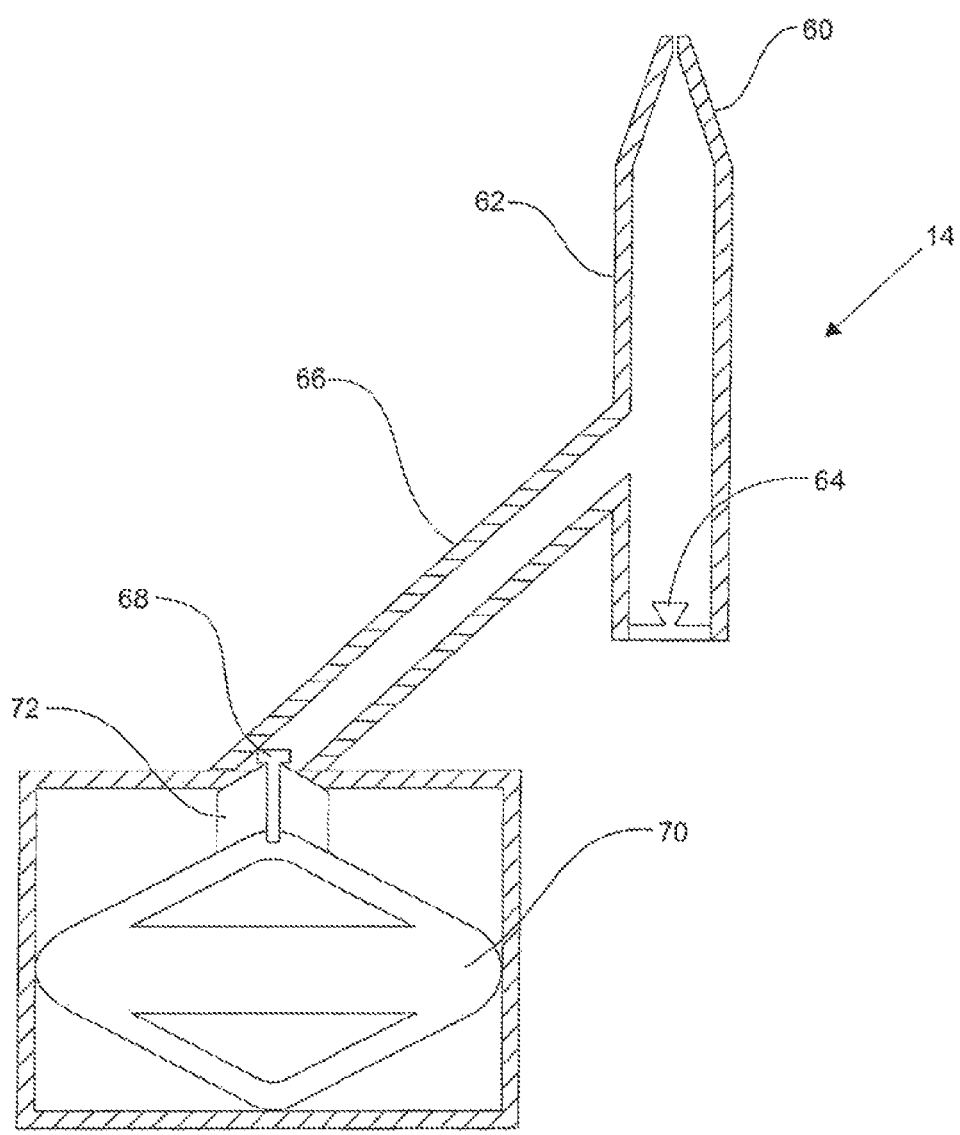
FIG. 6 is a cross-sectional perspective view of a piezo-electric air jet nozzle according to an embodiment of the invention.

In an embodiment, as shown in FIG. 6, the air jet nozzle 14 is driven by a piezoelectric transducer. A nozzle 60 is supported at a distal end of a hollow tube 62. At proximal end of the tube a small fixation LED 64 is supported in a housing for the patient to fixate their gaze. On a lateral branch of the tube 66 near the proximal end, a valve stem 68 is operatively connected to a piezoelectric device 70 to cause the valve stem to be moved axially toward and away from a valve seat 72 at the proximal end of the tube, between a seated and an unseated position. In the seated position, the valve stem engages the valve seat for preventing the flow of air from the housing therethrough. In the unseated position, the valve stem disengages from the valve seat and permits air to pass thereby through the hollow tube and out the nozzle.

The piezoelectric device is controlled so as to interrupt the air jet at the point of a sinus curve to obtain the desired burst. Interrupting of the jet too early results in cutting off too much air. Interrupting the air jet too late results in a decrease in air jet spike power. The air pressure in the piezo electric chamber casing is maintained at a fixed level using a ballast upstream from the piezo electric chamber.

The valve stem can be made of a variety of different materials including stainless steel, polyurethane or other plastics. In an embodiment, the valve stem is made of a high strength polyoxymethylene plastic, DELRIN®, which is made by E.I. Du Pont De Nemours and Company. Applicant has found that DELRIN® is particularly suitable for tight sealing of the exhaust, reducing noise in the system and avoiding rebounding of the valve stem after contact with the tube as well as reduced wear and tear. There appears to be less inertial effect and the amplitude observed in the spectral data is more constant allowing a very fast opening and closing of the airflow.

In one embodiment, the air jet is generated by an amplified piezoelectric actuator from Cedrat, model APA 100M, which has a stroke of 126 μM, blocked force of 234.5 N, and resonance frequency of 1900 Hz. In yet other embodiments the air jet is generated by a combination of 2 electromagnetic valves such as a set of 2 FESTO® MHJ1O valves in series. In yet another embodiment the air jet is generated by a magnetic valve, such as LUXALP® 30VR12A. This valve has the advantage that it can generate the pressure needed to vibrate the cornea at a much lower pressure than can other air jet valves, therefore allowing the use of a lower pressure generator than other valves described herein.

Wrist Sensor to Measure Peak IOP Due to Cardiac Systoly

In one embodiment of the method, system and apparatus a wrist sensor that measures systolic pulse is used. The wrist sensor enables the user to measure IOP at the peak of the ocular pulse, which provides a more accurate result. To achieve this synchronization, the correlation between the timing of the systolic and timing of the ocular pulse is determined, and the vibration measurement is launched by a signal that is sent from the wrist sensor to the air jet nozzle, so that the burst of air is released precisely at the peak of the ocular pulse.

Calculation of Intraocular Pressure

Once spectral data, typically amplitude and time, have been collected for the eye, the data can be correlated to IOP using an algorithm which has been created using known IOPs such as determined using Goldmann Applanation Tonometry (GAT) which is the "gold standard" for measuring IOP, as will be understood by one of skill in the art.

The correlation is based upon measures of intraocular pressure using GAT obtained from a statistically significant population of patients from different ethnic backgrounds having optimal central corneal thickness and minimal astigmatism.

The algorithm used to process the spectral data uses the vibration amplitude and time of onset measurements to estimate IOP. In some embodiments, gender and age of the subject are incorporated into the algorithm allowing more precise determination of the IOP reflecting the variation of IOP with age and gender.

The methods, systems and apparatus described herein may be used to measure IOP in mammalian or non-mammalian eye. For example, they may be used to measure IOP in humans, dogs, cats, chickens, pigeons, mice or rats (for example, animal models of glaucoma). As is apparent, this application would require identifying a suitable algorithm to be used with any particular animal, as described below. In a preferred embodiment the methods, systems and apparatus are used to measure IOP in a human eye.

This technology can also be developed for a self-tonometry device where the patient can measure IOP directly at home by looking directly into the nozzle at the correct distance which is detected by the device and automatically fires the air jet when the distance is measured to be correct.

Calculation of Corneal Elasticity

Once spectral data, typically amplitude and time, have been collected for the eye, the data can be correlated to corneal elasticity using an algorithm which has been created using known corneal elasticity such as determined using known elasticity from a model eye as will be understood by one of skill in the art.

The algorithm used to process the spectral data uses the vibration amplitude and time of onset measurements to estimate corneal elasticity. In some embodiments, gender and age of the subject are incorporated into the algorithm. The method, system and apparatus described detects a different biomechanical behavior, as manifest by corneal vibration response, between men and women.

Measurement of Scleral IOP

Figure 15:
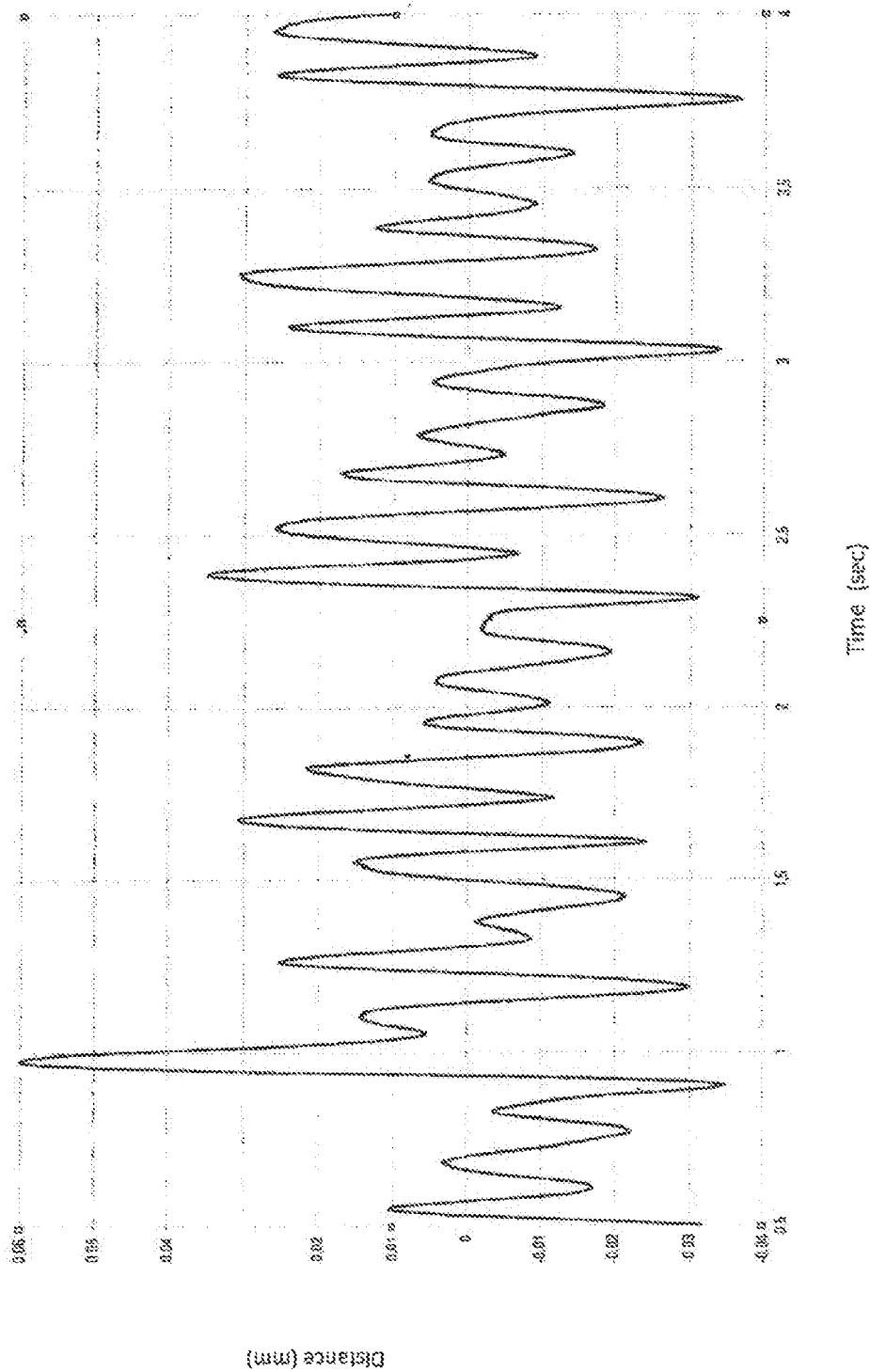
FIG. 15 shows ocular pulse as measured by the Chromatic Sensor described herein.
Figure 16A:
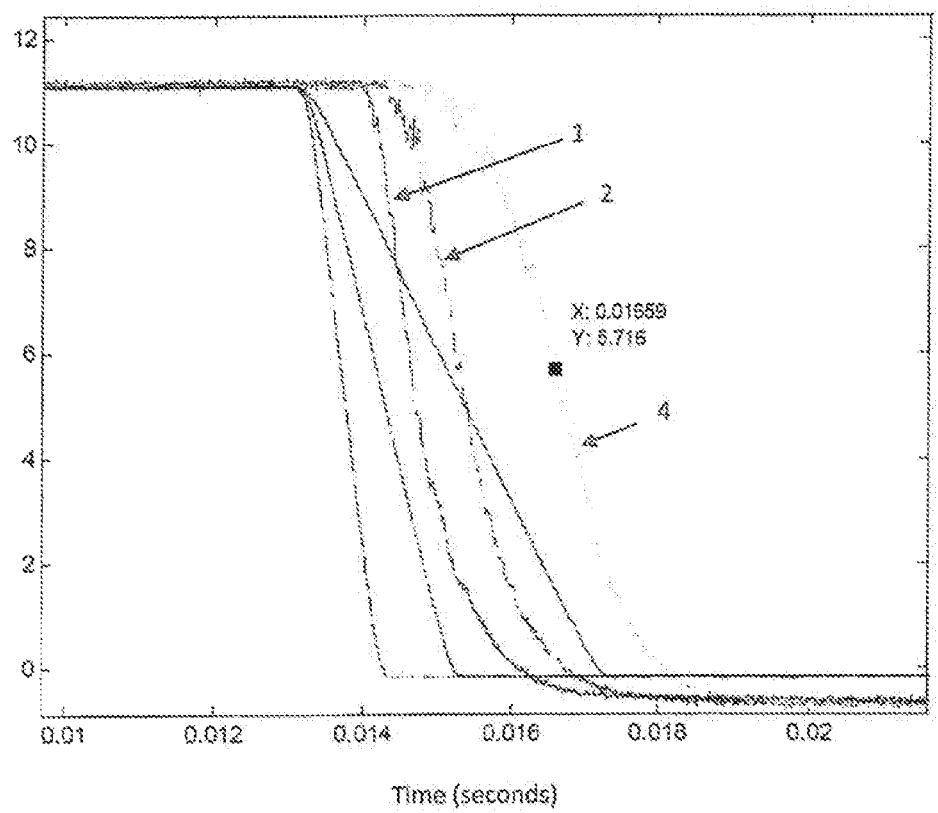
FIG. 16A shows the effect of a 1, 2 or 4 millisecond shut off speed of the piezoelectric air jet.
Figure 16B:
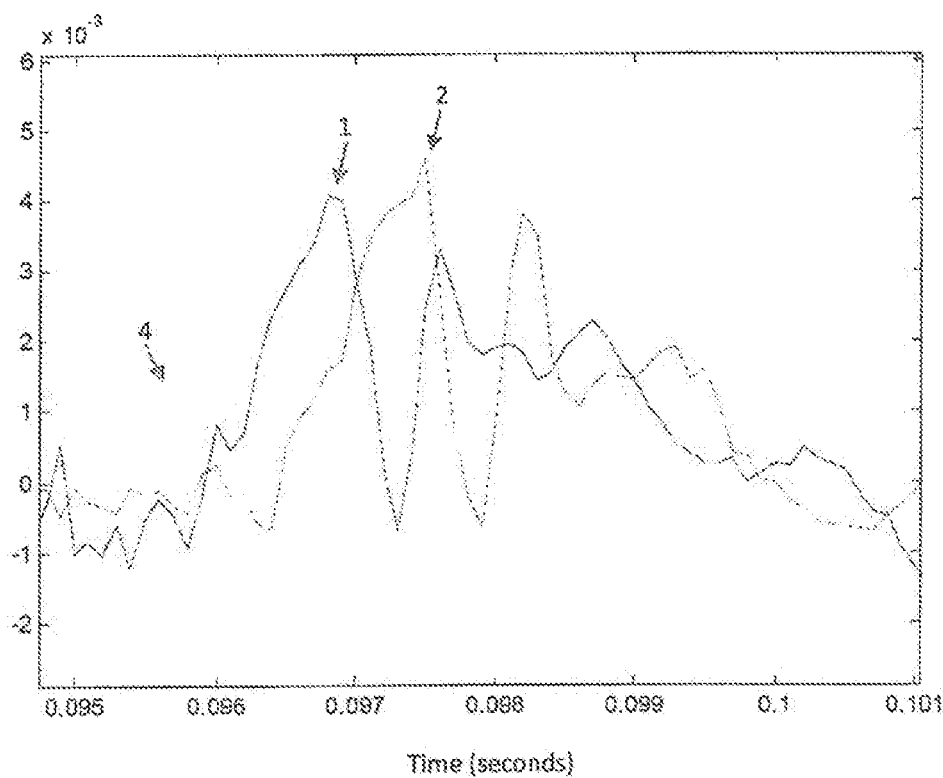
FIG. 16B shows the signal on the human eye at these three shut off speeds. This shows in 16A that at a 1 millisecond shutoff speed the steep curve generates a sharper response peak more visible than at a 2 millisecond shut off speed and that the response peak disappears at 4 milliseconds as seen in 16B.
Figure 17:
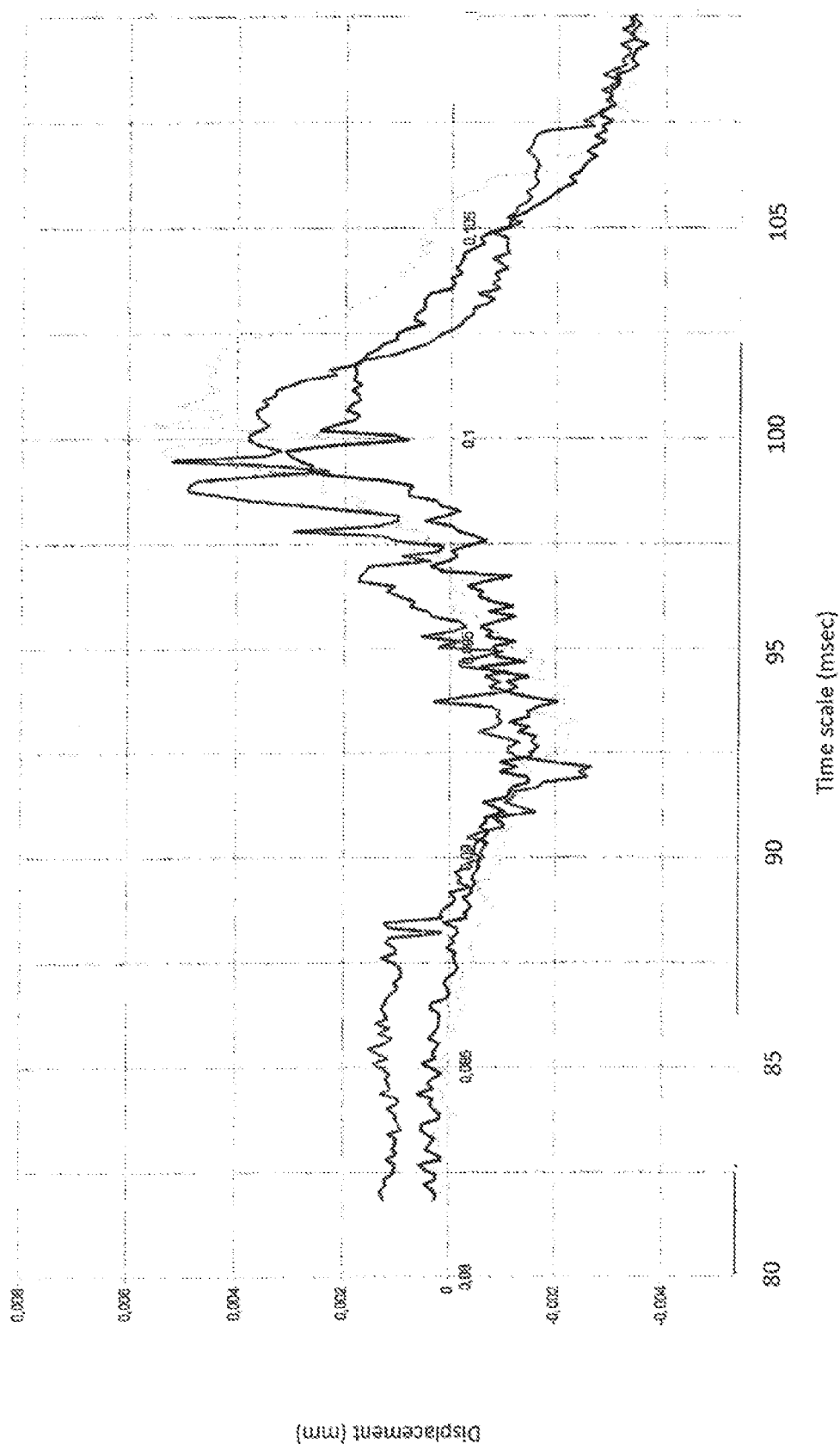
FIG. 17 shows the repeatability of the measurement using the Confocal Sensor, on a human eye. The test was performed three times, and the displacements were very similar using method described herein.

In some embodiments the tonometer is used to measure scleral IOP, which is useful in patients with corneal disease, corneal damage or an artificial cornea or keratoprosthesis or even possibly a corneal graft. Rather than measuring corneal vibration, scleral vibration is measured. The pressure measured by the GAT on the sclera is known to be about 9-13 mm Hg above that of the corneal measured IOP. To perform this measurement, the positions of the air jet and sensor do not change, nor do the methods of excitation and or the type of spectral data collected change. Patients are merely asked to look to the side at a side-fixating LED before the measurement is performed. In this method the pressure of the air jet is slightly higher than as for corneal measurements, and the algorithm is different as well Measurement of Ocular Pulse Amplitude The apparatus described herein may also be used to measure ocular pulse amplitude, as it is capable of measuring the movement of the cornea when the heart beats. In this method, no air jet excitation is used, and the sensor is merely turned on before or after measuring IOP to detect the movement of the cornea, measuring amplitude and frequency of the ocular pulse over a period of time. FIG. 15 shows the results obtained when using the apparatus to measure ocular pulse. For this, the sensor could be positioned anywhere on the surface of the cornea except near the limbus, where the corneal vibrations will be dampened by the junction of the thicker sclera. The axis of the incident light should still be normal to the surface of the cornea in order to receive sufficient backscattered light. This is preferably done with the confocal sensor.

Measurement of Corneal Thickness (Pachymetry)

The confocal sensor can also be used to measure distance from both the anterior and the posterior surface of the cornea using a narrower light beam and the difference between these can be calculated to be the corneal thickness at the point of measurement. The settings on the confocal sensor must be set to measure multiple distances as opposed to the distance to the first surface only. The difference between the distance measured by the sensor for the front and the back surfaces of the cornea is the corneal thickness.

Operation of an Embodiment of the Tonometer

In an embodiment of the tonometer shown in FIG. 1A, a tonometer comprises the sensor and air jet nozzle arranged as previously discussed. Two digital color cameras are positioned, symmetrically one on either side of the air jet nozzle placed on the optical axis in the horizontal plane and directed at the eye to ensure correct stereo positioning of the components of the tonometer relative to the eye. Further, an LED is situated in the air jet nozzle to provide a point of fixation for the patient. The components are mounted on a rigid support which can be rotated 90 degrees about the axis of the airjet nozzle in the vertical plane so as to permit obtaining measurements from both right and left eyes with minimal or no manipulation of the individual components and with asking the patient to move back and then use his other eye to fixate the LED inside the nozzle barrel. The Applicants have found that the best results are obtained when the axis of rotation is precisely about the micro air jet nozzle.

Figure 7:
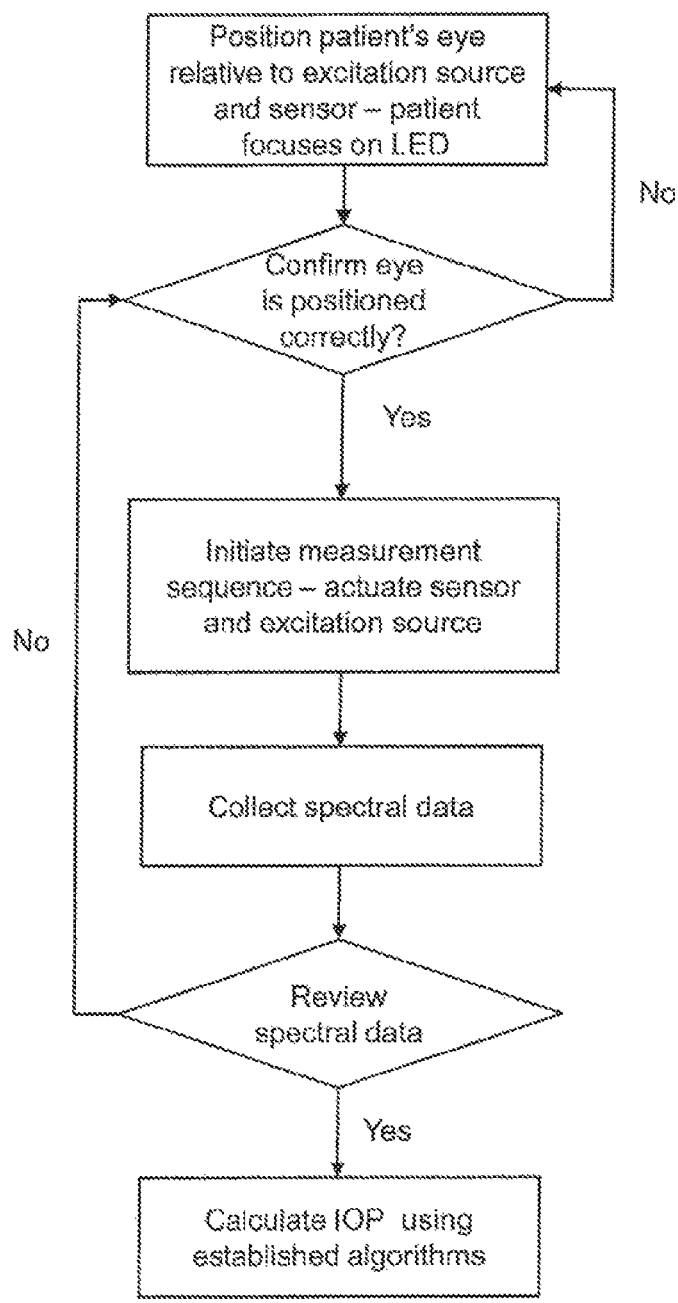
FIG. 7 is a flow chart illustrating a method of determining intraocular pressure using the system of FIG. 1.

As shown in FIG. 7, the tonometer according to an embodiment of the invention is positioned relative to the patient's eye, the patient focusing on the LED light to assist in aligning the optical axis of the eye relative to the tonometer components. The position of the eye is visualized by the operator and the operator adjusts the positioning of the tonometer in the X and Y and Z axes and confirms that the reflection of the fixation LED is at the center of the cross-hair etched in the camera image, thus positioning the air jet and sensor relative to the eye at acceptable angles. The launching of the measurement using the joystick button automatically moves the nozzle into position at 10 mm from the cornea, turns on the camera capture, turns on the sensor and starts the recording of the data. Timing and synchronization of the air pulse and measurements is important. Preferably the air pulse initiates about 20 msec after the onset of the launching of the measurement on the command joystick so as to allow filtering and data acquisition. The sensor signal is visualized to receive sufficient back scatter light at or above 10% using the Confocal Sensor. The Applicants have found that the minimum signal amplitude for the Micro-Epsilon® sensor calibration is about 10%, which provides a sufficient amount of reflected light to permit the sensor to make an accurate measurement.

The measurement is thus visually validated by the operator and can be repeated as needed, or moved to the fellow eye for measurements by rotation of the device by 90 degrees in the vertical plane. A series of three measurements are usually performed and the 2 closest measurements are automatically averaged, alternatively all 3 measurements are averaged. The microphone records the volume of the air burst and is precalibrated with the manometer, to thus ensure that the desired pressure is obtained with each air burst. This calibration is factory made prior to use and can be checked at periodic intervals.

The apex of the cornea of the eye is excited by an air burst over a total excitation time of about 15 ms or less, preferably about 5 ms. Therefore, the excitation has a duration of about 15 ms or less, preferably about 5 ms.

Simultaneously, the sensor is actuated for providing an incident beam at the eye and for capturing backscatter from the cornea to determine parameters related to displacement of eye, specifically amplitude and time of response. In some embodiments 2 or 3 short 1 millisecond pulses are automatically made one after the other to allow averaging for better signal to noise ratio.

The measurement sequence is initiated by the operator through a computer interface. Preferably the system is automated so that after adequate positioning of the air jet to centre it on the cornea, the launching of the measurement actuates the air jet function, sensor data acquisition, storage and processing. Preferably there is one integrated automatic launching of all functions to cut down the time between patient positioning, excitement by the air jet, camera recording and the confocal measurement.

Thereafter, the spectral data, which has been collected and confirmed to be complete and within acceptable limits, is converted to IOP using algorithms which have been established through correlation of the parameters related to displacement measured using an embodiment of the invention with known IOP determined using Goldman Applanation Tonometry. In one embodiment at least three measurements or more are taken, the eventual outlier is discarded and the two or three most constant values are averaged together (in the case where there is no outlier).

The process is then repeated for measurement of the intra-ocular pressure in the patient's fellow eye after repositioning of the tonometer through a simple rotation of the tonometer about the support structure.

EXAMPLES

Development of Algorithm

To develop and test the algorithm, two populations of patients were used, a discovery population to discover the algorithm and a validation population, to validate the algorithm. 200 patient samples, 400 eyes, several measures per eye were used, and ⅔ of the patients were randomly selected to be used as the discovery population, and ⅓ as the validation population. This was done 10 times in a row, by random draw separately for men and for women. For women the algorithm was developed and tested using 184 female eyes and 383 runs. 255 runs of measurements on female eyes were used to discover the algorithm representing ⅔ of runs and validation was performed on remaining ⅓ (128 runs) from different female eyes. This split was repeated 10 times at random.

On average using an algorithm including age and sex it was found that 95.5% of IOP measurements were within 5 mm of IOP measured using the reference Goldmann Applanation Tonometer (GAT) after averaging the two closest values (i.e. 4.5% were outside target range of 5 mm Hg from the reference GAT pressure).

For men the algorithm was developed and tested using 130 male eyes, 450 measurement runs. 300 runs were used to discover the algorithm representing ⅔ of runs and validation was performed on the remaining ⅓ (150 runs). This split was repeated 10 times at random.

On average using an algorithm including age and sex it was found that 92.8% of runs were within 5 mm Hg of measured IOP using GAT after averaging the 2 closest values (i.e. 7.2% are outside target range). It was noted that the male population had a broader distribution of IOP and may thus be more difficult to model using the algorithm.

Further studies on an additional 130 subjects (330 subjects total) have been performed. For women, therefore, a total of 590 runs of measurements on female eyes were used to develop and refine the algorithm, and validation was performed on 301 runs from different female eyes. For men a total of 442 runs were used to develop and refine the algorithm, and validation was performed on 370 runs from different male eyes.

For women in these additional studies, 98.6% of IOP measurements were within 5 mm of IOP measured using GAT, after averaging the two closest values (i.e. 1.4% were outside target range of 5 mm Hg pressure). For men in these additional studies, 97.4% of IOP measurements were within 5 mm of IOP measured using GAT, after averaging the two closest values (i.e. 2.6% were outside target range of 5 mm Hg pressure).

Introduction of the patient's pachymetry measurement did not affect the algorithm and did not improve it, and this suggests that the algorithm is not very sensitive to central corneal thickness (CCT). Indeed, further studies have shown that the method described herein is independent of CCT. Stratifying measurement differences between GAT and the method described herein as a function of CCT does not show any significant differences between positive errors (a measured value larger than GAT) and negative errors (a measured value less than GAT). Further, because the air pulse only causes a vibration of the cornea of about 1 micron, at the site of measurement, it stands to reason that the method is independent of CCT as compared to methods such as GAT, which applanate the cornea by about 100 microns (the cornea is on average about 530 microns thick).

Figure 20:
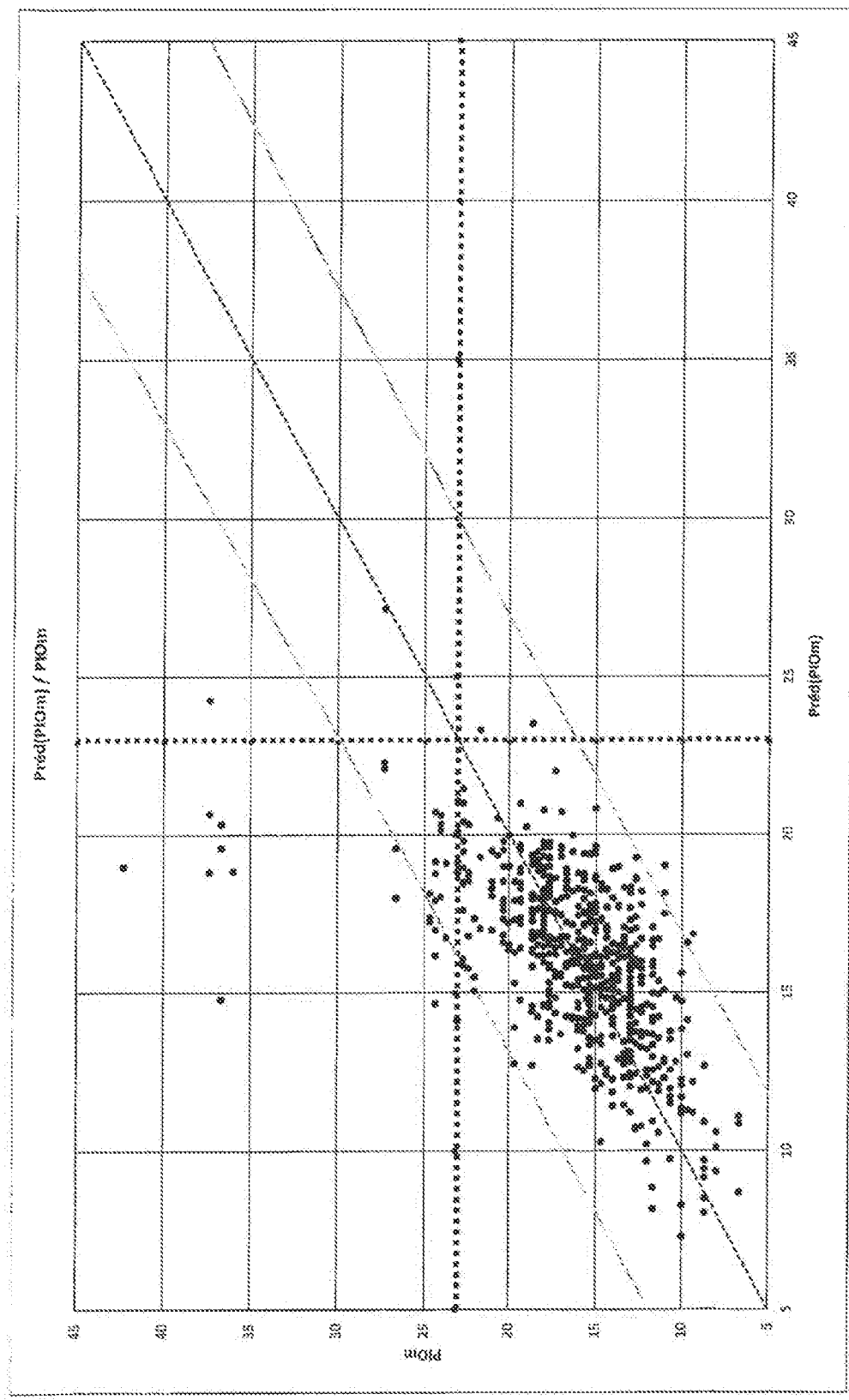
FIG. 20 is a scatter plot of mean IOP measured by the methods described herein (Pred PIOm) and mean IOP as measured by GAT (PIOm), in a female population sample. Mean IOP as measured by GAT is on the Y axis and mean IOP as measured by the methods described herein on the X axis. The lines on either side of the centre line delineate 95% confidence intervals.

FIG. 20 shows an example of the results for all measurement runs of the female population sample plotting mean IOP as measured by GAT on the Y axis, and mean IOP as measured by the methods described herein, on the X axis.

Comparison of Laser Sensor to a Commercial Industrial Self-Mixing Laser Vibrometer An embodiment of the Laser Sensor, referred to herein as "LASER", was compared to a conventional industrial Doppler laser vibrometer available from Polytec Inc. (SAS), herein referred to as "POLYTEC", for determining parameters related to vibration in an artificial target of known vibration amplitude and in the cornea of a pig eye.

Signals from both vibrometers were visualized and recorded using a LeCroy 44× Wavesurfer oscilloscope, available from LeCroy SA in Geneva.

Vibration was generated using a piezoelectric generator for amplitudes below about 1 micron and using an electromagnetic vibration generator for larger amplitudes. The servo-feedback loop of the LASER was arbitrarily locked to /=17.19 mA when pointed at the fixed target. The compensation circuit was also set to a predetermined value to maintain a constant drive current of the diode.

In a first test, the IR lasers were directed to a steel tip of the piezo-vibrator, the tip having a diameter of about 1 mm. Black paint was applied to the tip to reduce the reflection in order to permit the LASER to lock properly.

Ten separate runs were performed varying the frequency of vibration from 100 Hz to 1000 Hz and for known amplitudes between 0.3 um and 3.6 um. In most cases, the results from the LASER were proportional to those from the POLYTEC.

Figure 10:
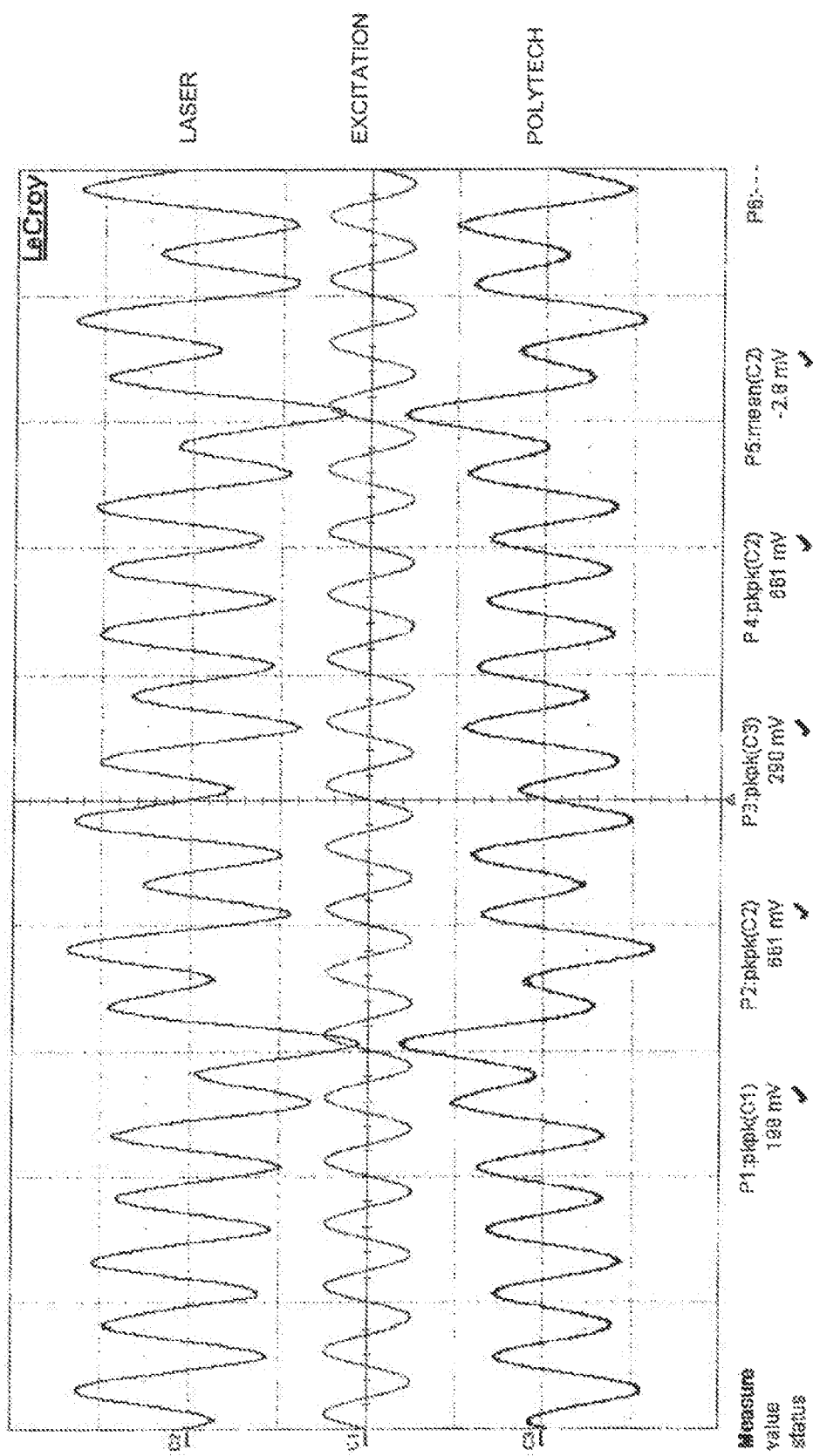
FIG. 10 is a LeCroy oscilloscope measurement of laser (top) and Polytec (lower graph) Doppler laser response to excitation (middle graph) of a piezo vibrator. Note the 200 mv/division scale for the Laser as opposed to 100 mv/division for the Polytec. C1: FLT, AC1M, 200 mV/div, 0.0 mV ofst; C2: FLT, AC1M, 200 mV/div, 400 mV; C3: FLT, AC1M, 100 mV/div, −200 mV; Tbase 0.0 ms, 2.00 ms/div, 100 kS, 5.0 MS/s; Shutter C1 HFR, Auto 0 mV, Edge Positive.
Figure 11:
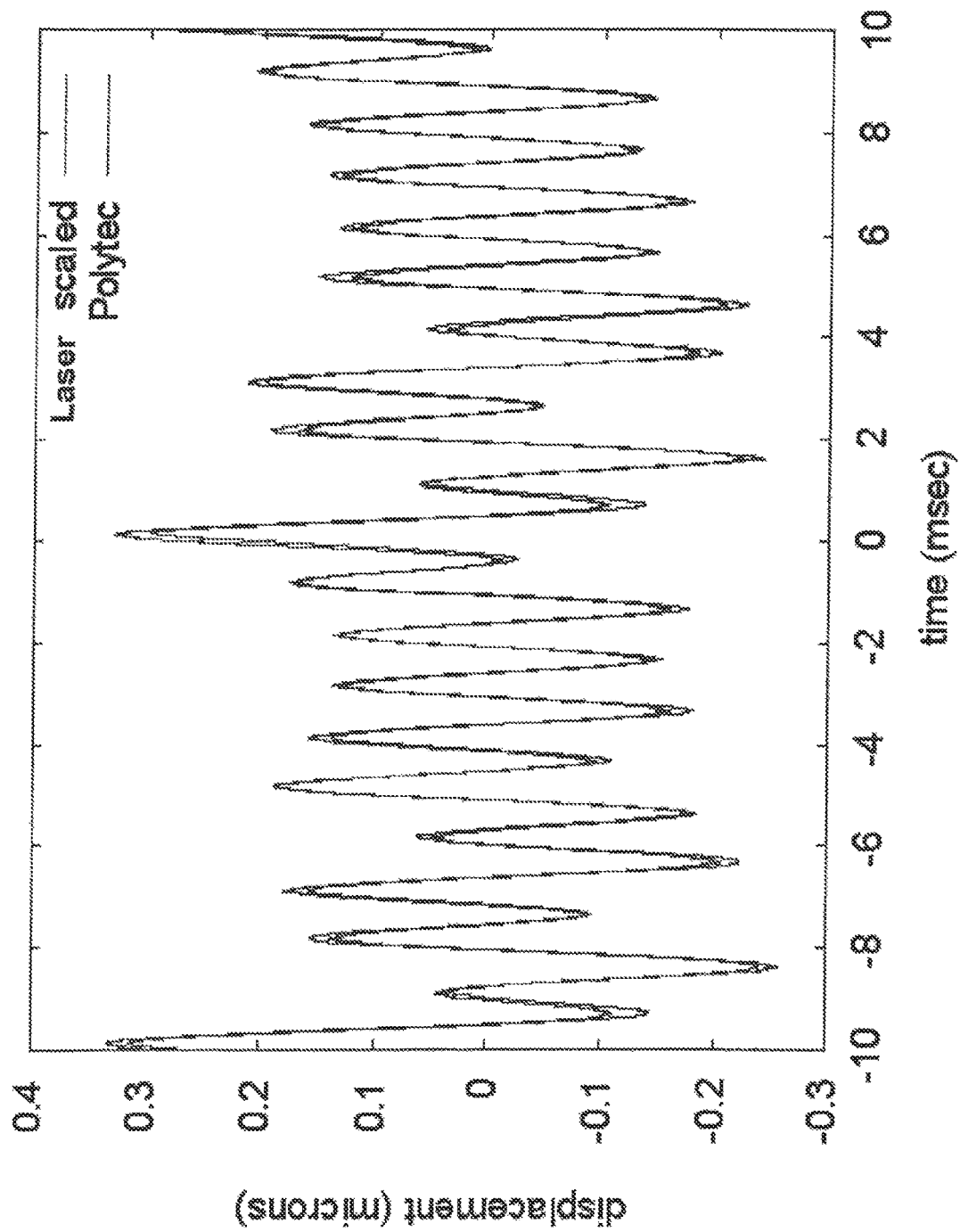
FIG. 11 is a laser displacement amplitude response scaled in microns.

A typical example of results generated using the electromagnetic vibrator are shown in FIG. 10. While the electromagnetic vibrator generally has a poor response, the poor response was evident for both vibrometers. As shown in FIG. 11 the signals can be made almost coincident using a single proportionality coefficient.

In a second ex vivo test, the vibration generators were replaced by a pig eye which was affixed to a support. The cornea of the eye was caused to vibrate using the piezo-vibrator which was gently pressed into the cornea about 3 mm from the centre.

Figure 12:
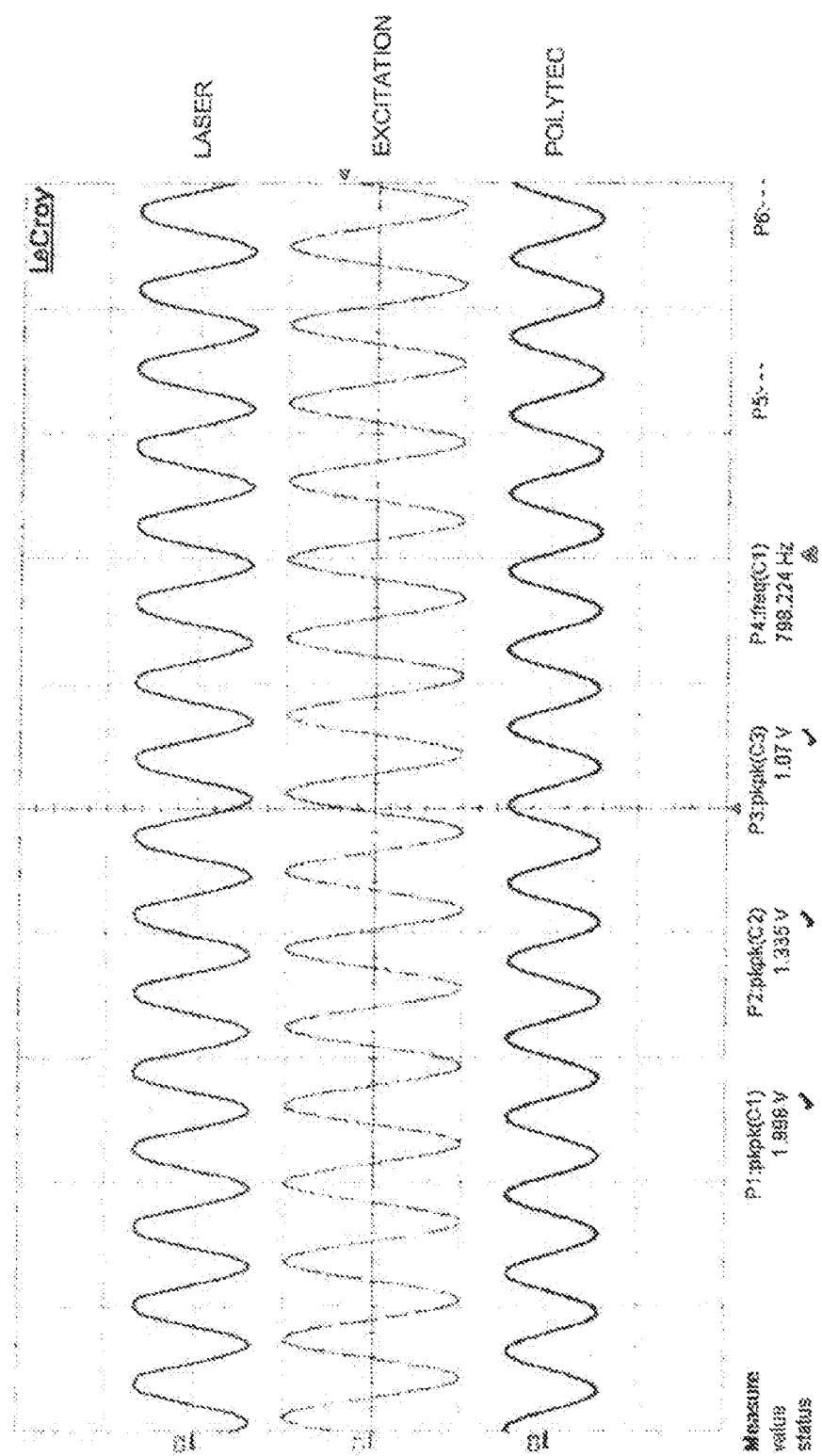
FIG. 12 is a LeCroy oscilloscope measurement of laser (top) and Polytec (lower graph) Doppler laser response to excitation (middle graph) on pig eye. Note again the higher response of the Laser than the Polytec. C1: FLT, AC1M, 1.0 V/div, 0.0 mV ofst; C2: FLT, AC1M, 1.00 V/div, 2.0000 V; C3: FLT, AC1M, 1.00 V/div, −2.000 V; Tbase 0.0 ms, 2.00 ms/div, 100 kS, 5.0 MS/s; Shutter C1 HFR, Stop 410 mV, Edge Positive.

Applicant has noted that, in the case of the POLYTEC, a small piece of reflective tape had to be affixed to the cornea in order to provide sufficient backscatter for the POLYTEC to obtain a reading. This was unnecessary in the LASER attesting to the sensitivity of the LASER to detect and utilize the limited backscatter from the naked cornea. The results are shown in FIG. 12. The upper trace is derived from the LASER and the lower trace is from the POLYTEC. The LASER was directed to a variety of positions on the cornea and with incident angles varying from 0° to about 20°.

Figure 13:
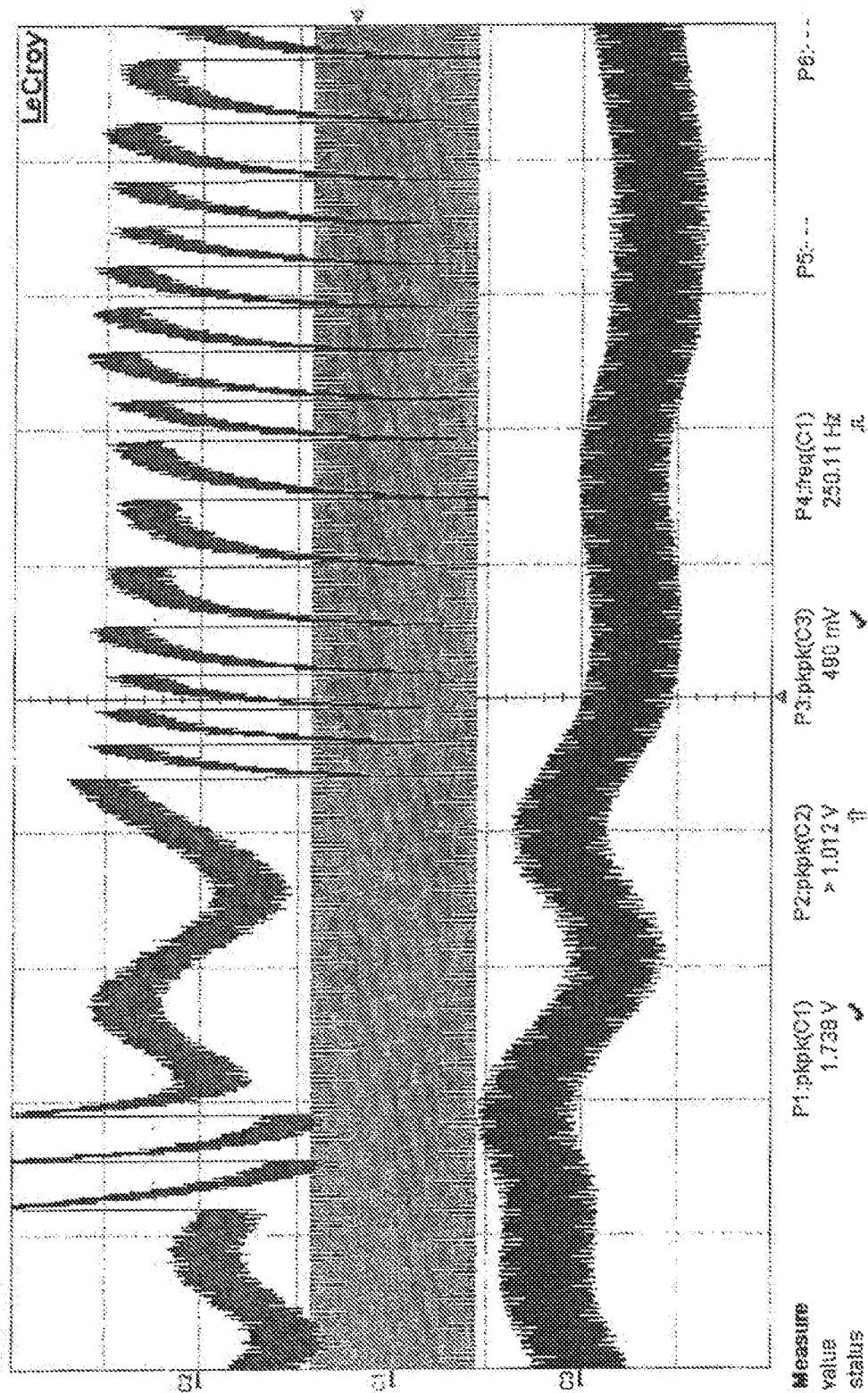
FIG. 13 is a LeCroy oscilloscope measurement of the Laser (top) and the Polytec (lower graph) Doppler laser response to excitation (middle graph) on pig eye showing phase jump related to eye movements. C1: FLT, AC1M, 1.00 V/div, 0.0 mV ofst; C2: FLT, AC1M, 200 mV/div, 400 mV; C3: FLT, AC1M, 200 mV/div, −400 mV; Tbase 0 ms, 200 ms/div, 100 kS, 50 kS/s; Shutter C1 DC, Stop 410 mV, Edge Positive.

FIG. 13 shows a typical result using the same conditions as described but over a longer time period. It was noted that large spikes appeared in the upper LASER trace which did not disappear when the vibrator drive was turned off. Applicant believes that this may relate to some eye movement and may also be related to the fact that the eye is dead and the cornea is oedematous and has no internal pressure.

Figure 14:
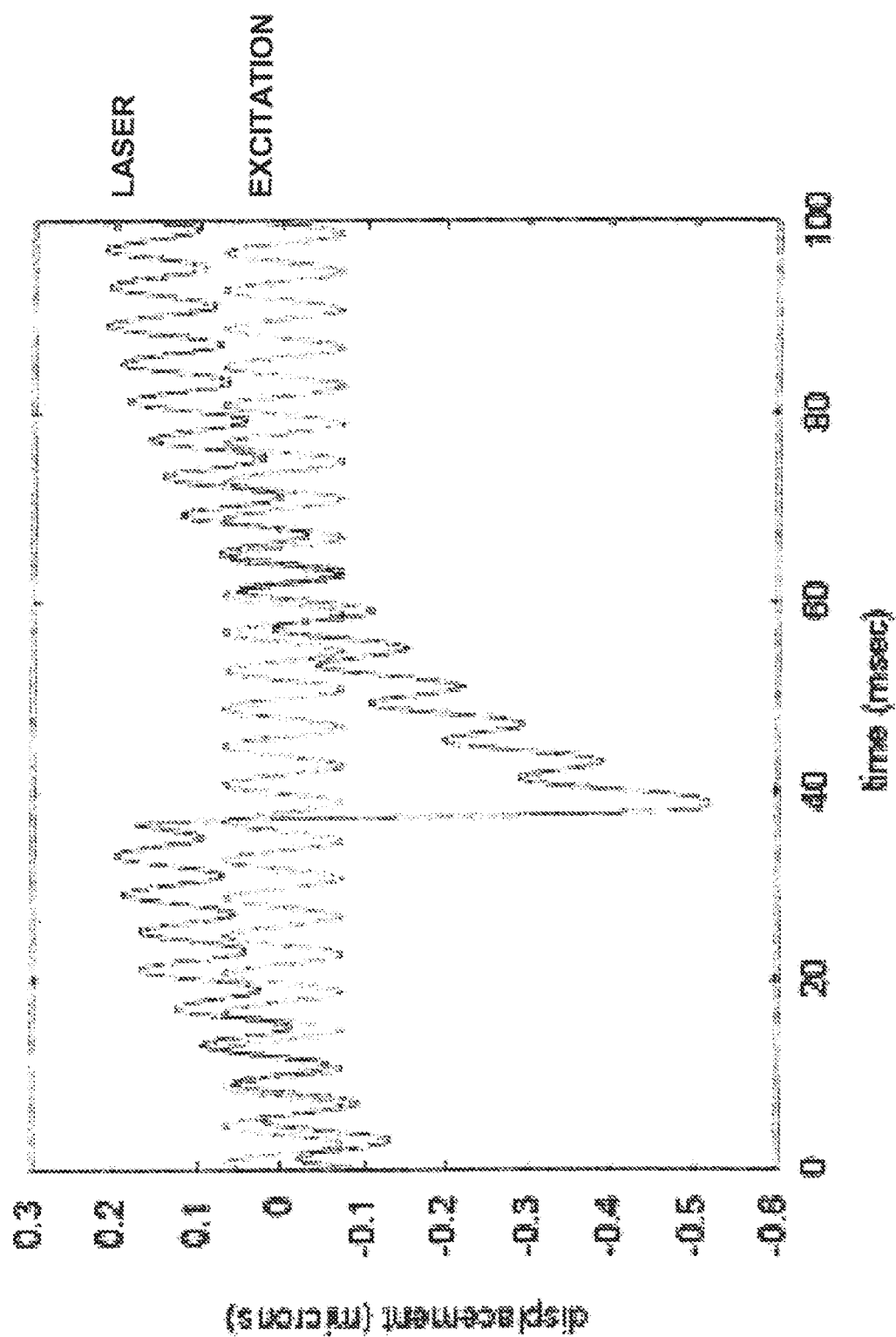
FIG. 14 is a LeCroy oscilloscope measurement of the Laser (top) response to excitation (lower graph) on pig eye showing phase jump related to eye movements on expanded time scale.

Further as shown in FIG. 14, it is apparent from the recordings in AC mode of the scope that for the LASER the low frequency part of the signals is filtered out. When the total displacement of the target is too large, the diode undergoes a "mode hop" which causes a jump in the signal. The recorded signals show that the LASER continues to correctly monitor the high frequency component. Applicant believes that this can be readily dealt with using means known to those of skill in the art, such as filters, a lock-in amplifier or a Fast Fourier Transformation (FFT) of the signal.

In conclusion, the tests show that the mean sensitivity of the LASER is about −0.83 umN and the dynamic range is at least 2 um. It was later shown that in the present embodiment the laser sensitivity extends well beyond 5 microns. Further, the tests show that the LASER is sensitive to vibrations of a naked pig-eye cornea which the conventional POLYTEC is not.

Modulation of the Laser Sensor Signal

A patient's spontaneous slow eye movements perturb the laser measurement which cannot differentiate phase from current amplitude. These movements can be filtered out using a modulation signal mixed into the laser measurement signal followed by demodulation of such in order to remove the signal perturbations.

Figure 18:
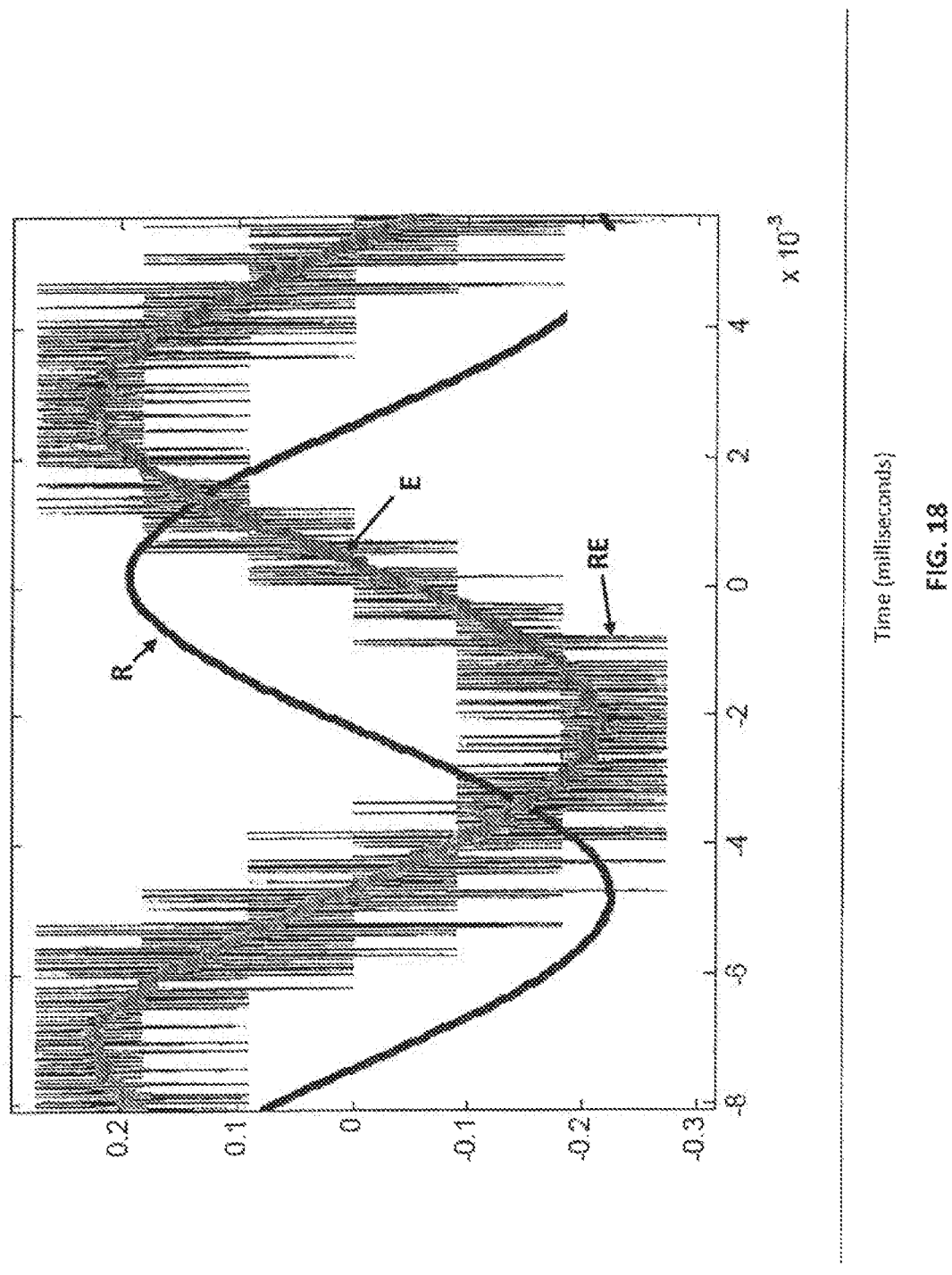
FIG. 18 is an example of modulation at 100 Hz. It shows that patient's eye movements can be filtered out using a modulation signal mixed into the laser measurement signal, followed by demodulation of such in order to remove the signal perturbations. The lines show real target position (R), raw estimate (RE) and estimated target position (E).
Figure 19:
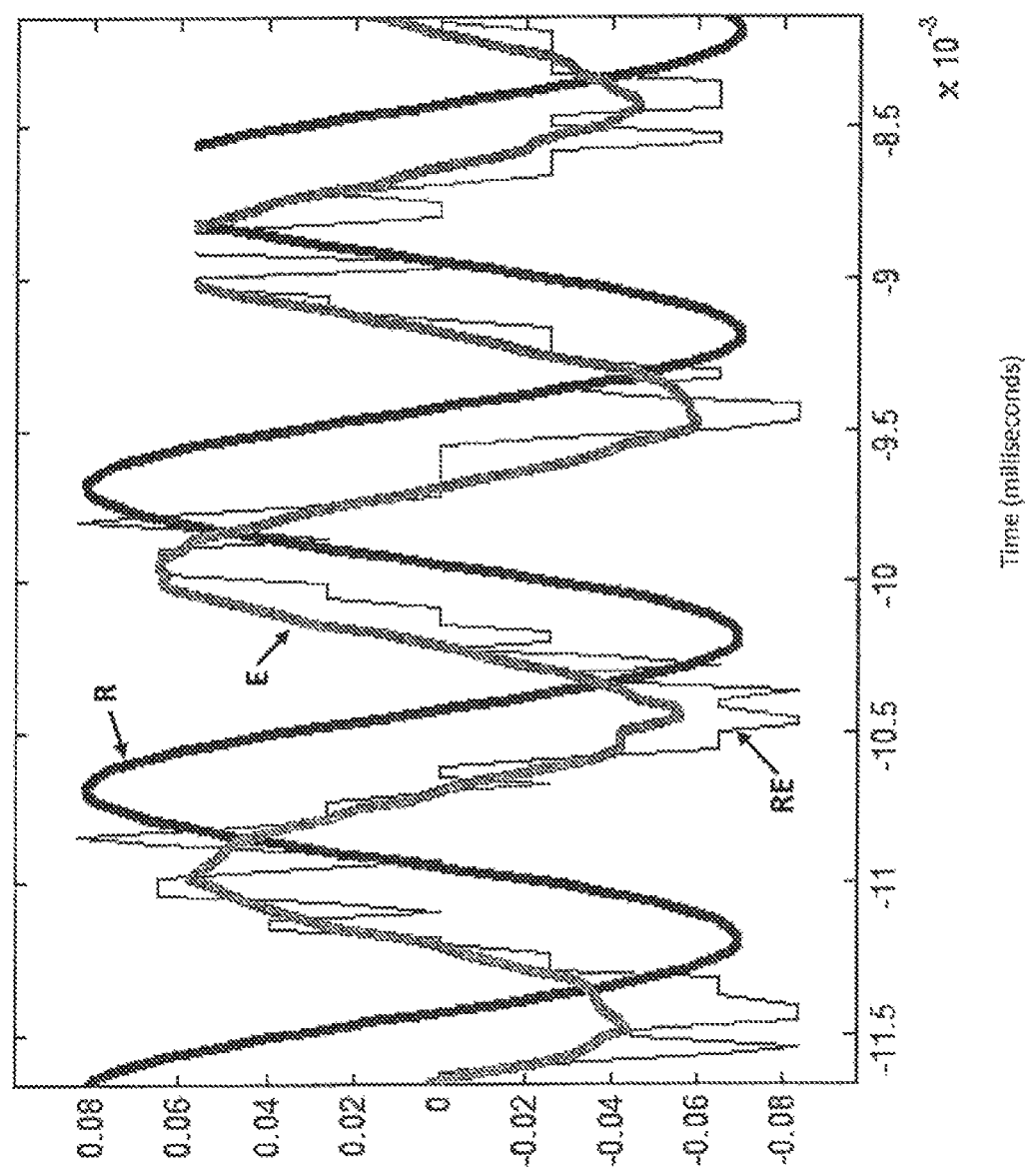
FIG. 19 is modulation at 1000 Hz for a Doppler simulation. It shows that patient eye movements can be filtered out using a modulation signal mixed into the laser measurement signal, followed by demodulation of such in order to remove the signal perturbations. The lines show real target position (R), raw estimate (RE) and estimated target position (E).

FIG. 18 is an example of modulation at 100 Hz. A different multi entry oscilloscope needs to be used for higher frequency. The Applicants have achieved validation of this signal modulation using a piezo electric-actuated mirror at 500 Hz. The use of a density of 0.6 does not impair processing of the moving target signal even though the signal strength is attenuated 30 times by the glass density. FIG. 19 is an example of modulation at 1000 Hz in a Doppler simulation.

I claim:

1. A system for measuring a vibrational response in an eye for determination of ocular parameters comprising:
    an air jet nozzle directed at an anatomical apex of a cornea of the eye along an optical axis extending from the apex to a center of a pupil, configured for providing an excitation stimulus at a single frequency to cause vibration in the eye; and
    a sensor positioned and configured for emitting incident light that is directed along an axis distinct from the optical axis to a point on the eye removed a distance from the apex, said sensor configured for receiving backscatter light from the point to measure the vibrational response of the eye to the excitation stimulus, said sensor positioned to both emit incident light and receive backscatter light at the same position,
    wherein the incident light approaches a surface of the eye at an angle that is perpendicular to a surface tangent of the eye at the point.

2. The system of claim 1, wherein the incident light from the sensor approaches the surface at an angle of 28+/−4 degrees between the optical axis and the axis of the incident light.

3. The system of claim 1, wherein the measuring of the vibrational response comprises measuring both a temporal response and an amplitude response to the excitation stimulus,
    optionally wherein the measuring of the vibrational response comprises measuring during and immediately after the excitation stimulus.

4. The system of claim 1, further comprising a circuit board for calculating the ocular parameters,
    wherein an ocular parameter of the ocular parameters is intraocular pressure and the system further comprises a first algorithm for determining the intraocular pressure from the vibrational response of the cornea, wherein the first algorithm incorporates both age and gender of a patient, or gender alone, and/or
    wherein an ocular parameter of the ocular parameters is corneal elasticity and the system further comprises a second algorithm for determining the corneal elasticity from the vibrational response of the cornea.

5. The system of claim 2 wherein the point is on a temporal side of the apex of the eye,
    optionally 2 to 6 mm from the apex,
    optionally 5 to 6 mm from the apex.

6. The system of claim 2, wherein the measuring of the vibrational response comprises measuring both a temporal response and an amplitude response to the excitation stimulus,
    optionally wherein the measuring of the vibrational response comprises measuring during and immediately after the excitation stimulus.

7. The system of claim 2, further comprising a circuit board for calculating the ocular parameters,
wherein an ocular parameter of the ocular parameters is intraocular pressure and the system further comprises a first algorithm for determining the intraocular pressure from the vibrational response of the cornea, wherein the first algorithm incorporates both age and gender of a patient, or gender alone, and/or
wherein an ocular parameter of the ocular parameters is corneal elasticity and the system further comprises a second algorithm for determining the corneal elasticity from the vibrational response of the cornea.

8. The system of claim 6, further comprising a circuit board for calculating the ocular parameters,
wherein an ocular parameter of the ocular parameters is intraocular pressure and the system further comprises a first algorithm for determining the intraocular pressure from the vibrational response of the cornea, wherein the first algorithm incorporates both age and gender of a patient, or gender alone, and/or
wherein an ocular parameter of the ocular parameters is corneal elasticity and the system further comprises a second algorithm for determining the corneal elasticity from the vibrational response of the cornea.

9. The system of claim 1, wherein the system further comprises a camera disposed on the optical axis.

10. The system of claim 2, wherein the incident light from the sensor approaches the surface on a temporal side of the apex of the eye.

11. The system of claim 2, wherein the incident light from the sensor approaches the surface at an angle of about 45 degrees below a horizontal equator of the cornea at the apex.

12. The system of claim 10, wherein the incident light from the sensor approaches the surface at an angle of about 45 degrees below a horizontal equator of the cornea at the apex.

13. The system of claim 12, further comprising a circuit board for calculating the ocular parameters,
wherein an ocular parameter of the ocular parameters is intraocular pressure and the system further comprises a first algorithm for determining the intraocular pressure from the vibrational response of the cornea, wherein the first algorithm incorporates both age and gender of a patient, or gender alone, and/or
wherein an ocular parameter of the ocular parameters is corneal elasticity and the system further comprises a second algorithm for determining the corneal elasticity from the vibrational response of the cornea.

14. A system for measuring a vibrational response in an eye for determination of corneal thickness comprising:
an air jet nozzle directed at an anatomic apex of a cornea of the eye along an optical axis extending from the apex to a center of a pupil, configured for providing an excitation stimulus at a single frequency to cause vibration in the eye; and
a sensor configured for emitting incident light that is directed along an axis distinct from the optical axis, to a point on the eye removed a distance from the apex, said sensor configured for receiving backscatter light from the point to measure the vibrational response of the eye to the excitation stimulus, said sensor positioned to both emit incident light and receive backscatter light at the same position,
wherein the incident light approaches a surface of the eye perpendicular to a surface tangent at the point.

15. The system of claim 14, wherein the system further comprises a camera disposed on the optical axis.

16. A method for measuring a vibrational response in an eye of a patient, for determining ocular parameters of the eye comprising:
positioning an air jet nozzle configured to direct an excitation stimulus at a single frequency to an anatomical apex of a cornea of the eye along an optical axis extending from the apex to a center of a pupil of the eye;
positioning a sensor configured to both direct incident light along an axis distinct from the optical axis to a point on the eye removed a distance from the apex and to detect backscatter light from the point wherein the incident light approaches a surface of the eye at an angle that is perpendicular to the surface tangent of the eye at the point;
exciting vibration in the eye with the excitation stimulus;
directing incident light from the sensor to the point on the eye at an angle that is perpendicular to a surface tangent of the eye at the point; and
detecting backscatter light from the point on the eye with said sensor, to measure the vibrational response of the eye to the excitation stimulus.

17. The method of claim 16, wherein the measuring of the vibrational response comprises measuring both a temporal response and an amplitude response to the excitation stimulus, and
optionally wherein the measuring of the vibrational response comprises measuring during and immediately after the excitation stimulus.

18. The method of claim 16 further comprising determining intraocular pressure from the vibrational response of the cornea using a first algorithm that incorporates both age and gender of the patient or gender alone, and
optionally further comprising determining corneal elasticity from the vibrational response of the cornea using a second algorithm.

19. The method of claim 16 further comprising determining intraocular pressure from the vibrational response of a sclera of the eye, using a third algorithm that incorporates both age and gender of the patient.

20. The method of claim 16, further comprising measuring an ocular pulse amplitude by measuring peak and trough eye pressure during a heartbeat.

* * * * *